United States Patent
Al-Ali

(10) Patent No.: US 9,668,703 B2
(45) Date of Patent: *Jun. 6, 2017

(54) BIDIRECTIONAL PHYSIOLOGICAL INFORMATION DISPLAY

(71) Applicant: Masimo Corporation, Irvine, CA (US)

(72) Inventor: Ammar Al-Ali, San Juan Capistrano, CA (US)

(73) Assignee: Masimo Corporation, Irvine, CA (US)

( * ) Notice: Subject to any disclaimer, the term of this patent is extended or adjusted under 35 U.S.C. 154(b) by 96 days.

This patent is subject to a terminal disclaimer.

(21) Appl. No.: 14/444,705

(22) Filed: Jul. 28, 2014

(65) Prior Publication Data

US 2015/0025406 A1    Jan. 22, 2015

Related U.S. Application Data

(63) Continuation of application No. 12/904,823, filed on Oct. 14, 2010, now Pat. No. 8,790,268.

(Continued)

(51) Int. Cl.
*A61B 5/08* (2006.01)
*A61B 5/00* (2006.01)
(Continued)

(52) U.S. Cl.
CPC .............. *A61B 5/7445* (2013.01); *A61B 5/08* (2013.01); *A61B 5/0816* (2013.01);
(Continued)

(58) Field of Classification Search
CPC ............................. A61B 5/742; A61B 5/7425
See application file for complete search history.

(56) References Cited

U.S. PATENT DOCUMENTS

| | | |
|---|---|---|
| 3,682,161 A | 8/1972 | Alibert |
| 4,127,749 A | 11/1978 | Atoji et al. |
| | (Continued) | |

FOREIGN PATENT DOCUMENTS

| | | |
|---|---|---|
| CA | 2262236 | 4/2008 |
| EP | 0716628 | 12/1998 |
| | (Continued) | |

OTHER PUBLICATIONS

U.S. Appl. No. 12/904,775, filed Oct. 14, 2010, Fechter et al.

(Continued)

*Primary Examiner* — Meredith Weare
(74) *Attorney, Agent, or Firm* — Knobbe, Martens & Olson & Bear LLP

(57) ABSTRACT

A patient monitor for displaying a physiological signal can include a visual element having a middle portion indicative of a transition in the physiological signal between physiological states. The visual element can also include first and second extremity portions, the first extremity portion extending from the middle portion in a first direction and the second extremity portion extending from the middle portion in a second direction. The visual element can also include an actionable value indicator to specify a value about the middle portion and the first and second extremity portions. The patient monitor can also include a processor configured to cause the value indicator to actuate in both the first and second directions according to changes in the physiological signal.

20 Claims, 15 Drawing Sheets

Related U.S. Application Data

(60) Provisional application No. 61/252,083, filed on Oct. 15, 2009, provisional application No. 61/331,087, filed on May 4, 2010, provisional application No. 61/288,843, filed on Dec. 21, 2009, provisional application No. 61/290,436, filed on Dec. 28, 2009.

(51) Int. Cl.
*A61B 7/00* (2006.01)
*G06F 19/00* (2011.01)

(52) U.S. Cl.
CPC .......... *A61B 5/6833* (2013.01); *A61B 5/7435* (2013.01); *A61B 7/003* (2013.01); *G06F 19/3406* (2013.01); *G06F 19/3418* (2013.01)

(56) References Cited

U.S. PATENT DOCUMENTS

| | | | |
|---|---|---|---|
| 4,326,143 | A | 4/1982 | Guth et al. |
| 4,537,200 | A | 8/1985 | Widrow |
| 4,884,809 | A | 12/1989 | Rowan |
| 5,033,032 | A | 7/1991 | Houghtaling |
| 5,143,078 | A | 9/1992 | Mather et al. |
| D353,195 | S | 12/1994 | Savage et al. |
| D353,196 | S | 12/1994 | Savage et al. |
| D359,546 | S | 6/1995 | Savage et al. |
| D361,840 | S | 8/1995 | Savage et al. |
| D362,063 | S | 9/1995 | Savage et al. |
| 5,448,996 | A | 9/1995 | Bellin et al. |
| D363,120 | S | 10/1995 | Savage et al. |
| 5,602,924 | A | 2/1997 | Durand et al. |
| 5,738,106 | A | 4/1998 | Yamamori et al. |
| 6,106,481 | A | 8/2000 | Cohen |
| 6,241,683 | B1 | 6/2001 | Macklem et al. |
| 6,248,083 | B1 | 6/2001 | Smith et al. |
| 6,368,283 | B1 | 4/2002 | Xu et al. |
| 6,430,437 | B1 | 8/2002 | Marro |
| 6,486,588 | B2 | 11/2002 | Doron et al. |
| 6,517,497 | B2 | 2/2003 | Rymut et al. |
| 6,595,316 | B2 | 7/2003 | Cybulski et al. |
| 6,661,161 | B1 | 12/2003 | Lanzo et al. |
| 6,725,074 | B1* | 4/2004 | Kastle ............ A61B 5/14551 600/322 |
| 7,096,060 | B2 | 8/2006 | Arand et al. |
| 7,239,905 | B2 | 7/2007 | Kiani-Azarbayjany et al. |
| 8,491,489 | B2* | 7/2013 | Shin ............ A61B 5/0878 600/529 |
| 8,523,781 | B2* | 9/2013 | Al-Ali ............ A61B 5/08 600/529 |
| 8,641,631 | B2* | 2/2014 | Sierra ............ A61B 5/02 600/483 |
| 8,790,268 | B2* | 7/2014 | Al-Ali ............ A61B 5/08 340/573.1 |
| 2002/0161291 | A1 | 10/2002 | Kianl et al. |
| 2002/0193670 | A1 | 12/2002 | Garfield et al. |
| 2003/0015368 | A1 | 1/2003 | Cybulski et al. |
| 2003/0163033 | A1 | 8/2003 | Dekker |
| 2004/0133087 | A1 | 7/2004 | Ali et al. |
| 2004/0158162 | A1 | 8/2004 | Narimatsu |
| 2005/0033128 | A1* | 2/2005 | Ali ............ A61B 5/1455 600/323 |
| 2005/0272987 | A1 | 12/2005 | Kiani-Azarbayjany et al. |
| 2006/0047215 | A1 | 3/2006 | Newman et al. |
| 2006/0094943 | A1* | 5/2006 | Van Slyke ......... A61B 5/14551 600/323 |
| 2006/0144397 | A1 | 7/2006 | Wallace et al. |
| 2006/0184052 | A1* | 8/2006 | Iwasawa ............ A61B 5/022 600/485 |
| 2006/0238333 | A1 | 10/2006 | Welch et al. |
| 2007/0135725 | A1 | 6/2007 | Hatlestad |
| 2007/0167855 | A1* | 7/2007 | Shin ............ A61B 5/0878 600/533 |
| 2007/0185397 | A1 | 8/2007 | Govari et al. |
| 2007/0282212 | A1* | 12/2007 | Sierra ............ A61B 5/0205 600/529 |
| 2008/0039735 | A1* | 2/2008 | Hickerson ............ A61B 5/7445 600/532 |
| 2008/0076972 | A1 | 3/2008 | Dorogusker et al. |
| 2008/0188733 | A1* | 8/2008 | Al-Ali ............ A61B 5/0205 600/364 |
| 2008/0188760 | A1* | 8/2008 | Al-Ali ............ A61B 5/14551 600/507 |
| 2009/0018429 | A1 | 1/2009 | Saliga et al. |
| 2009/0093687 | A1 | 4/2009 | Telfort et al. |
| 2009/0170664 | A1* | 7/2009 | Shirasaki ............ A61B 5/0816 482/13 |
| 2009/0187065 | A1 | 7/2009 | Basinger |
| 2009/0299157 | A1 | 12/2009 | Telfort et al. |
| 2010/0094096 | A1* | 4/2010 | Petruzzelli ........... A61B 5/0205 600/300 |
| 2010/0274099 | A1 | 10/2010 | Telfort et al. |
| 2011/0224567 | A1 | 9/2011 | Al-Ali |
| 2011/0288431 | A1 | 11/2011 | Alshaer et al. |

FOREIGN PATENT DOCUMENTS

| | | |
|---|---|---|
| EP | 0659058 | 1/1999 |
| EP | 1207536 | 5/2002 |
| GB | 2358546 | 11/1999 |
| JP | 6214898 | 1/1987 |
| JP | 01-309872 | 6/1998 |
| JP | 10-155755 | 6/1998 |
| JP | 2001-50713 | 5/1999 |
| JP | 2003-329719 | 11/2003 |
| WO | WO 94/05207 | 3/1994 |
| WO | WO 94/13207 | 6/1994 |
| WO | WO 95/29632 | 11/1995 |
| WO | WO 99/53277 | 10/1999 |
| WO | WO 00/10462 | 3/2000 |
| WO | WO 01/34033 | 5/2001 |
| WO | WO 01/78059 | 10/2001 |
| WO | WO 01/97691 | 12/2001 |
| WO | WO 02/03042 | 1/2002 |
| WO | WO 03/058646 | 7/2003 |
| WO | WO 03/087737 | 10/2003 |
| WO | WO 2004/000111 | 12/2003 |
| WO | WO 2004/004411 | 1/2004 |
| WO | WO 2005/096931 | 10/2005 |
| WO | WO 2005/099562 | 10/2005 |
| WO | WO 2008/017246 | 2/2008 |
| WO | WO 2008/148172 | 12/2008 |
| WO | WO 2009/137524 | 11/2009 |

OTHER PUBLICATIONS

U.S. Appl. No. 12/904,789, filed Oct. 14, 2010, Telfot, Valery et al.
U.S. Appl. No. 12/904,836, filed Oct. 14, 2010, Al-Ali et al.
U.S. Appl. No. 12/904,823, filed Oct. 14, 2010, Al-Ali et al.
U.S. Appl. No. 12/904,890, filed Oct. 14, 2010, Al-Ali et al.
U.S. Appl. No. 12/904,907, filed Oct. 14, 2010, Telfort et al.
U.S. Appl. No. 12/904,931, filed Oct. 14, 2010, Telfort et al.
U.S. Appl. No. 12/904,938, filed Oct. 14, 2010, Telfort et al.
U.S. Appl. No. 12/905,036, filed Oct. 14, 2010, Kiani et al.
U.S. Appl. No. 12/905,384, filed Oct. 15, 2010, Al-Ali et al.
U.S. Appl. No. 12/905,449, filed Oct. 15, 2010, Al-Ali et al.
U.S. Appl. No. 12/905,489, filed Oct. 15, 2010, Weber et al.
U.S. Appl. No. 12/905,530, filed Oct. 15, 2010, Al-Ali et al.
U.S. Appl. No. 12/960,325, filed Dec. 3, 2010, Al-Ali, Ammar et al.
Analog Devices, 12-Bit Serial Input Multiplying D/A Converter, Product Data Sheet, 2000.
Eldor et al., "A device for monitoring ventilation during anaesthesia; the paratracheal audible respiratory monitor", Canadian Journal of Anaesthesia, 1990, vol. 9, No. 1, p. 95-98.
International Search Report & Written Opinion, PCT Application PCT/US2010/052758, Feb. 10, 2011; 12 pages.
International Search Report & Written Opinion, PCT Application PCT/US2010/058981, Feb. 17, 2011; 11 pages.
International Search Report, PCT Application PCT/CA2003/000536, Dec. 11, 2003; 2 pages.

(56) References Cited

OTHER PUBLICATIONS

International Search Report and Written Opinion issued in application No. PCT/US2010/052756 on Feb. 6, 2012.
International Search Report, PCT Application PCT/US2009/069287, Mar. 30, 2010; 7 pages.
Sierra et al., Monitoring Respiratory Rate Based on Tracheal Sounds. First Experiences, Proceedings of the 26th Annual Int'l Conf. of the IEEE EMBS (Sep. 2004), 317-320.
Welch Allyn, ECG ASIC, Product Data Sheet, 2001.

* cited by examiner

BIDIRECTIONAL PHYSIOLOGICAL INFORMATION DISPLAY

RELATED APPLICATIONS

This application is a continuation of U.S. patent application Ser. No. 12/904,823 filed Oct. 14, 2010, and entitled "Bidirectional Physiological Information Display," which claims priority from U.S. Provisional Patent Application No. 61/252,083 filed Oct. 15, 2009, and entitled "Displaying Physiological Information," U.S. Provisional Patent Application No. 61/288,843 filed Dec. 21, 2009, and entitled "Acoustic Respiratory Monitor," U.S. Provisional Patent Application No. 61/290,436 filed Dec. 28, 2009, and entitled "Acoustic Respiratory Monitor," and from U.S. Provisional Patent Application No. 61/331,087, filed May 4, 2010, entitled "Acoustic Respiration Display," the disclosures of which are hereby incorporated by reference in their entirety.

This application also relates to the following U.S. patent applications, the disclosures of which are incorporated in their entirety by reference herein:

| App. No. | Filing Date | Title | Attorney Docket |
|---|---|---|---|
| 60/893,853 | Mar. 08, 2007 | MULTI-PARAMETER PHYSIOLOGICAL MONITOR | MCAN.014PR |
| 60/893,850 | Mar. 08, 2007 | BACKWARD COMPATIBLE PHYSIOLOGICAL SENSOR WITH INFORMATION ELEMENT | MCAN.015PR |
| 60/893,858 | Mar. 08, 2007 | MULTI-PARAMETER SENSOR FOR PHYSIOLOGICAL MONITORING | MCAN.016PR |
| 60/893,856 | Mar. 08, 2007 | PHYSIOLOGICAL MONITOR WITH FAST GAIN ADJUST DATA ACQUISITION | MCAN.017PR |
| 12/044,883 | Mar. 08, 2008 | SYSTEMS AND METHODS FOR DETERMINING A PHYSIOLOGICAL CONDITION USING AN ACOUSTIC MONITOR | MCAN.014A |
| 61/141,584 | Dec. 30, 2008 | ACOUSTIC SENSOR ASSEMBLY | MCAN.030PR |
| 61/252,076 | Oct. 15, 2009 | ACOUSTIC SENSOR ASSEMBLY | MCAN.030PR2 |
| 12/643,939 | Dec. 21, 2009 | ACOUSTIC SENSOR ASSEMBLY | MCAN.030A |
| 61/313,645 | Mar. 12, 2010 | ACOUSTIC RESPIRATORY MONITORING SENSOR HAVING MULTIPLE SENSING ELEMENTS | MCAN.033PR2 |
| 12/904,931 | Oct. 14, 2010 | ACOUSTIC RESPIRATORY MONITORING SENSOR HAVING MULTIPLE SENSING ELEMENTS | MCAN.033A |
| 12/904,890 | Oct. 14, 2010 | ACOUSTIC RESPIRATORY MONITORING SENSOR HAVING MULTIPLE SENSING ELEMENTS | MCAN.033A2 |
| 12/904,938 | Oct. 14, 2010 | ACOUSTIC RESPIRATORY MONITORING SENSOR HAVING MULTIPLE SENSING ELEMENTS | MCAN.033A3 |
| 12/904,907 | Oct. 14, 2010 | ACOUSTIC PATIENT SENSOR | MCAN.033A4 |
| 61/252,099 | Oct. 14, 2009 | ACOUSTIC RESPIRATORY MONITORING SYSTEMS AND METHODS | MCAN.034PR |
| 12/904,789 | Oct. 14, 2010 | ACOUSTIC RESPIRATORY MONITORING SYSTEMS AND METHODS | MCAN.034A |
| 61/252,062 | Oct. 15, 2009 | PULSE OXIMETRY SYSTEM WITH LOW NOISE CABLE HUB | MCAN.035PR |
| 61/265,730 | Dec. 01, 2009 | PULSE OXIMETRY SYSTEM WITH ACOUSTIC SENSOR | MCAN.035PR3 |
| 12/904,775 | Oct. 14, 2010 | PULSE OXIMETRY SYSTEM WITH LOW NOISE CABLE HUB | MCAN.035A |
| 12/905,036 | Oct. 14, 2010 | PHYSIOLOGICAL ACOUSTIC MONITORING SYSTEM | MCAN.046A |
| 61/391,098 | Oct. 08, 2010 | ACOUSTIC MONITOR | MCAN-P001 |

Many of the embodiments described herein are compatible with embodiments described in the above related applications. Moreover, some or all of the features described herein can be used or otherwise combined with many of the features described in the applications listed above.

BACKGROUND

Monitoring of respiratory activity in a patient is desirable in clinical situations since death or brain damage can occur within minutes of respiratory failure. As respiratory failure can be difficult to predict, continuous monitoring of respiratory activity is particularly beneficial in high-risk situations. Appropriate monitoring equipment saves lives. Moreover, respiratory monitoring equipment can also be useful for non-critical care, including exercise testing and different types of cardiac investigations.

A patient's respiratory activity can be monitored by an acoustic respiratory monitor. An acoustic respiratory monitor can include one or more acoustic sensors that can be positioned on a patient's body to obtain acoustic respiratory information from a patient for analysis. In some cases, the acoustic sensors may be positioned to detect tracheal sounds, which can be heard at the suprasternal notch or at the lateral neck near the pharynx or at another location on the patient.

SUMMARY

In certain embodiments, a patient monitor for displaying a physiological signal includes a visual element having a middle portion indicative of a transition in the physiological signal between physiological states. The visual element can also include first and second extremity portions, the first extremity portion extending from the middle portion in a first direction and the second extremity portion extending from the middle portion in a second direction. The visual element can also include an actionable value indicator to specify a value about the middle portion and the first and second extremity portions. The patient monitor can also include a processor configured to cause the value indicator to actuate in both the first and second directions according to changes in the physiological signal.

In certain embodiments, a method of displaying physiological information, implemented by a processor, includes providing a value of a physiological parameter to a display of a patient monitor, where the physiological parameter value reflects physiological information obtained from a physiological sensor coupled to a patient. The method can further include calculating a freshness of the physiological parameter value and adjusting an output associated with the parameter value based at least in part on the calculated freshness.

In certain embodiments, a method of displaying physiological information, implemented by a processor, includes outputting a value of a physiological parameter to a display of a patient monitor, where the physiological parameter value reflects physiological information obtained from a physiological sensor coupled to a patient. The method can further include outputting a signal quality indicator reflecting a quality of the physiological information obtained from the physiological sensor, determining whether the value of the physiological parameter is valid, and adjusting the signal quality indicator responsive to said determination.

In certain embodiments, a method of displaying physiological information, implemented by a processor, can include providing a value of a physiological parameter to a display of a patient monitor, where the physiological parameter value reflects physiological information obtained from a physiological sensor coupled to a patient. The method can further include determining whether the value of the physiological parameter is valid, freezing an output associated with the physiological parameter value, calculating a freshness of the physiological parameter value, in response to said freezing, and adjusting the output associated with the parameter value based at least in part on the calculated freshness.

Further, in some embodiments, a method is provided for displaying physiological information on a physiological monitor that can be coupled to a patient sensor that can detect a physiological signal. The method, implemented by a processor, can include outputting a value indicator to a display of the patient monitor, expanding the value indicator in two directions simultaneously in response to increasing values in a parameter measured from the physiological signal, and contracting the value indicator opposite the two directions simultaneously in response to falling values of the measured parameter.

In certain embodiments, a method of displaying physiological information on a physiological monitor, implemented by a processor, can include receiving a physiological signal from a sensor coupled to a patient, where the physiological signal reflects a physiological parameter of the patient. The method can further include activating a visual indicator of a visual element to cause the visual indicator to illuminate from a central region outwards toward both a first end region and a second end region of the visual element and then inwards from the first and second end regions toward the central region, responsive to changes in the physiological parameter.

A physiological monitor can include, in certain embodiments, a processor that can receive physiological information from one or more sensors coupled with a patient and a display having a visual element for representing values of a physiological parameter responsive to the physiological information. The visual element can include a middle portion representing an initial position, first and second extremity portions, the first extremity portion extending from the middle portion in a first direction, and the second extremity portion extending from the middle portion in a second direction, and a value indicator that can illuminate starting from the initial position and expanding both to the first and second extremity portions, followed by contracting at least partway toward the middle portion, responsive to changes in the physiological parameter.

For purposes of summarizing the disclosure, certain aspects, advantages and novel features of the inventions have been described herein. It is to be understood that not necessarily all such advantages can be achieved in accordance with any particular embodiment of the inventions disclosed herein. Thus, the inventions disclosed herein can be embodied or carried out in a manner that achieves or optimizes one advantage or group of advantages as taught herein without necessarily achieving other advantages as can be taught or suggested herein.

BRIEF DESCRIPTION OF THE DRAWINGS

Throughout the drawings, reference numbers can be re-used to indicate correspondence between referenced elements. The drawings are provided to illustrate embodiments of the inventions described herein and not to limit the scope thereof.

DETAILED DESCRIPTION

Systems and methods of visually communicating information about physiological signals (e.g., respiratory signals) to an observer are described herein. In one embodiment, a physiological monitoring system includes one or more sensors to detect a physiological signal from a patient. For example, the physiological signal can be an acoustic representation of a respiratory signal detected by an acoustic sensor in the vicinity of a patient. The physiological monitoring system can also include a display for communicating information about the physiological signal to an observer, as well as a processor for processing the physiological signal and controlling the display.

In some embodiments, the display includes a visual element with a value indicator for visually communicating a value associated with a physiological signal to an observer. The value indicator can have an initial position and can expand or contract in a first portion of the visual element during a first physiological state. The first physiological state can, for example, correspond to patient inspiration (or inhalation). The value indicator can expand or contract in a second portion of the visual element during a second physiological state, which can correspond, for example, to patient expiration (or exhalation). In other embodiments, the value indicator expands from a reference position in at least two directions simultaneously, the reference position being representative of a transition between first and second physiological states, such as patient inspiration and expiration.

Multidirectional Display

Figure 1:
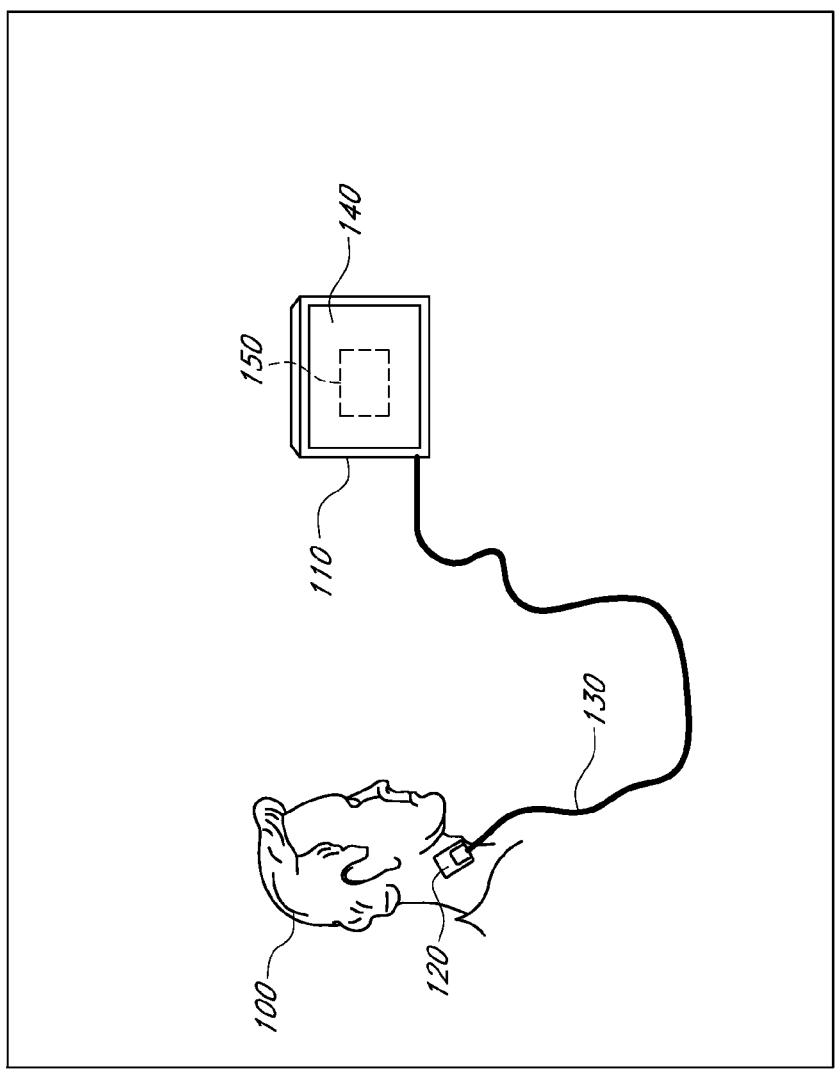
FIG. 1 is a depiction of an embodiment of a patient monitoring system for acquiring, processing, and displaying physiological information (e.g., respiratory-related information)

FIG. 1 illustrates a respiratory monitoring system 105 for monitoring the respiratory activity of a patient 100. The respiratory monitoring system 105 includes a respiratory monitor 110 communicatively coupled to a sensor 120. The sensor 120 is positioned on the patient's body to detect respiratory sounds. In one embodiment, the sensor 120 includes a piezoelectric crystal transducer to transform sound vibrations in the patient's body into electrical signals. Other types of sensors can also be used. The resulting electrical respiratory signal can be transferred to the respiratory monitor 110 via electrical leads 130, by wireless transmission, or any other appropriate method. Various sensors and monitors adaptable to be used with any of the embodiments described herein, have been described in the following applications and issued patents: U.S. Provisional No. 60/893,853, filed Mar. 8, 2007; U.S. Provisional No. 60/893,850, filed Mar. 8, 2007; U.S. Provisional No. 60/893, 858, filed Mar. 8, 2007; U.S. Provisional No. 60/893,856, filed Mar. 8, 2007; U.S. application Ser. No. 11/547,570, filed Oct. 6, 2006; U.S. application Ser. No. 12/643,939, filed Dec. 21, 2009, and U.S. Pat. No. 6,661,161 (see also FIG. 10). Each of these references is hereby incorporated by reference in its entirety.

The respiratory monitor 110 can include circuitry to convert the respiratory signal into a digital format, as well as a processor (not shown) to analyze the respiratory signal. For example, the respiratory signal can be processed or analyzed with a Fourier transform or other mathematical transform to determine or analyze the frequency content of the signal. The signal can also be time-averaged, filtered, amplified, or otherwise conditioned or analyzed using the processor. For example, the processor can be configured to determine a patient's inspiratory time, expiratory time, inspiratory to expiratory ratio, inspiratory flow, expiratory flow, tidal volume, minute volume, apnea duration, breath sounds—including rales, rhonchi, or stridor, changes in breath sounds, etc. Regardless of whether the acquired signal is in analog or digital form, has been conditioned, transformed, or otherwise analyzed or altered, it can generally be referred to as a respiratory signal or acoustic signal throughout this disclosure.

Once the respiratory signal has been acquired by the sensor 120 and transferred to the respiratory monitor 110, the signal, or aspects of it, can be communicated to an observer by a visual element 150 of the respiratory monitor display 140. FIGS. 2-9 illustrate various embodiments of the visual element 150. While certain embodiments can be described primarily in the context of displaying respiratory signals, the same principles can be applied to display other types of physiological signals as well, such as heart rate, blood pressure, blood oxygen saturation, etc.

Figure 2:
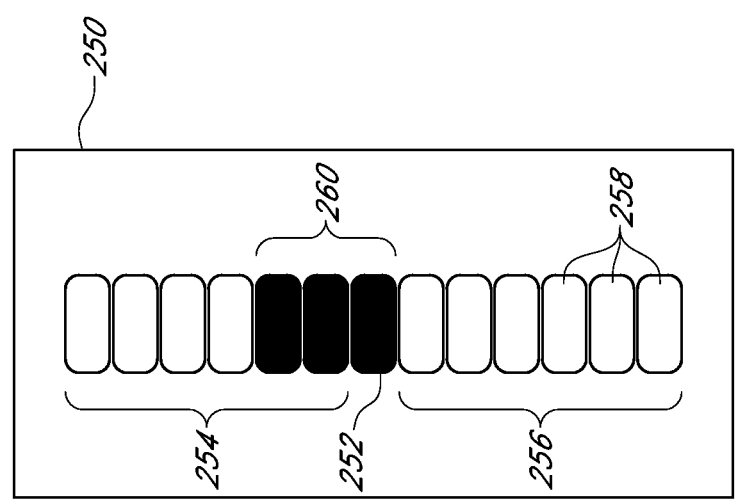
FIG. 2 is a schematic representation of an embodiment of a visual element for use with the system of FIG. 1 to display a physiological signal (e.g., a respiratory signal)

FIG. 2 illustrates a visual element 250, in this case a bar graph, which can be displayed on a patient monitor to communicate to a user certain aspects of a physiological signal. In some embodiments, the visual element 250 is a color or monochrome segmented LED, LCD, and/or a bit-mapped type display. Other types of displays are also possible and can be used equally well. The bar graph 250 can include a plurality of segments 258, or any other type of sub-division. In certain embodiments, each segment 258 has an inactive state, such as a dark state, and an active state, such as one or more lit states of varying brightness, or vice versa. In certain embodiments, the lit state includes one or more colors. The segments 258 can be transitioned between dark and lit states, or between colors, in order to convey information about a physiological signal to a user.

One or more segments 258 can make up a middle portion 252 of the bar graph 250. Other groupings of segments 258 can make up a first extremity portion 254 (e.g., an upper extremity portion) and a second extremity portion 256 (e.g., a lower extremity portion) of the bar graph 250. In some embodiments, the upper 254 and lower 256 extremity portions of the bar graph 250 are each indicative of relatively larger magnitudes of values of an acquired physiological signal, or some characteristic derived from the acquired physiological signal, than is the middle portion 252. In other embodiments, however, one of the extremity portions may represent lesser magnitudes than the other, while the middle portion can represent magnitudes between the greater and lesser magnitudes represented by the extremity portions.

In some embodiments, the bar graph 250 is calibrated. For example, the bar graph 250 can be calibrated in units of energy in a physiological signal or, in the case of respiratory signals, in units of respiratory volume. Other calibration units are also possible. In some embodiments, a calibration scale is explicitly indicated on or near the bar graph 250 to communicate quantitative information to an observer about the strength of a physiological signal. In certain embodiments, the calibration scale of the bar graph 250 is reconfigurable, whether manually or automatically, according to the ranges of values present in the physiological signal. For example, in the case of a respiratory signal of a patient with relatively shallow breathing, the dynamic range of the calibration scale can be decreased so that the signal extends over a greater portion of the bar graph 250. In cases where a patient is breathing very deeply, the dynamic range of the calibration scale can be increased to avoid clipping of the visual depiction of the respiratory signal.

The bar graph 260 can also include a value indicator 260 which actuates in time, e.g. by transitioning bar graph segments 258 between dark and lit states, as the physiological signal changes. In some embodiments, the value indicator 260 is a grouping of one or more segments 258, the number of which changes as the value indicator 260 actuates, of the visual element 250. The value indicator 260 can be indicative of any characteristic of an acquired physiological signal and can actuate anywhere along the bar graph 250. For example, the value indicator 260 can represent the amplitude of a physiological waveform at a point in time, the amplitude of a selected frequency range of the physiological signal over a specified time period, or the intensity of the physiological signal at a point in time.

Other characteristics of a physiological signal can also be represented by the value indicator 260. For example, in the case of a respiratory signal, the value indicator 260 can represent an indication of the acoustic volume of breathing sounds picked up by an acoustic sensor 120. In some embodiments, an indication of the acoustic volume of a patient's respiratory sounds is related to the amplitude of a relatively low frequency envelope of a sound waveform detected by the sensor 120. The value indicator 260 can also represent the respiratory rate of a patient, the depth of breathing, or any other type of information related to a respiratory signal, including a quality of a respiratory signal (see FIG. 11).

It should be understood that while FIG. 2 illustrates one embodiment of a value indicator, many different types of value indicators can be used in various embodiments. The value indicator 260 illustrated in FIG. 2 is one that is well-suited to embodiments where the visual element 150 includes a bar graph. However, other types of value indicators may be better-suited to other types of visual elements 150. The term "value indicator," in addition to having its ordinary meaning, is intended to refer to any type of visual indicator capable of graphically communicating to a user a value associated with a physiological signal, including amplitude, frequency, etc. related to a physiological signal.

In certain embodiments, the value indicator 260 expands in length to indicate increases in the value or magnitude of a selected characteristic of the physiological signal. Conversely, the value indicator may contract in length to indicate decreases in the value or magnitude of the signal. While the value indicator 260 is shown in FIG. 1 as only extending from the middle portion 252 into the upper extremity portion 254 of the bar graph 250, in other embodiments, it may extend into both extremity portions 254, 256 simultaneously.

The value indicator 260 can change colors and/or flash as it actuates as an additional method of conveying information to a user. For example, the value indicator 260 could be displayed in red for relatively small values or magnitudes of a respiratory signal, which may correspond to shallow breathing by a patient. In other embodiments, the value indicator 260 flashes between dark and lit states to indicate shallow breathing. If the patient's breathing increases to normal levels, however, the value indicator 260 may change to green or cease flashing. Similar methods of changing colors of the value indicator 260 or causing it to flash can be used to indicate other aspects of a respiratory signal, such as if the patient's respiratory rate drops below a predetermined or user-selected threshold.

In certain embodiments, the middle portion 252 of the bar graph indicates a transition between two or more different physiological states. The states can, for example, be any detectable or distinct physiological event, phase, or condition. In some, but not all, embodiments, a transition between physiological states represents the occurrence or presence of a distinct physiological event or condition, rather than simply a greater or lesser degree of a continuing physiological event or condition. In embodiments where the bar graph 260 is used to communicate values of an acquired patient respiratory signal, the middle portion 252 of the bar graph 250 can indicate a transition between inspiration and expiration in the patient's respiratory activity, each of which is a distinct phase of respiratory activity. In other words, when a value in the middle portion 252 of the bar graph is marked, it is an indication of the patient transitioning between inspiration and expiration. In other embodiments, the middle portion 252 marks a transition of a physiological signal between normal and abnormal values. For example, the middle portion 252 could mark where a patient's blood oxygen saturation transitions between healthy and dangerous levels.

Figure 3:
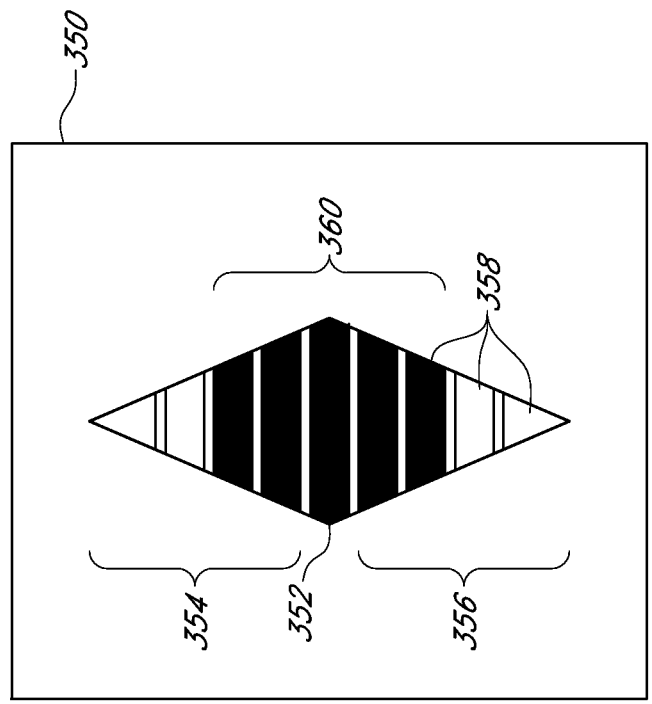
FIG. 3 is a schematic representation of an embodiment of a visual element for use with the system of FIG. 1 to display a physiological signal (e.g., a respiratory signal)

In addition to the generally rectangular shaped bar graph shown in FIG. 2, other bar graph shapes are also possible. For example, FIG. 3 illustrates a diamond-shaped visual element 350. Much like the bar graph 250, the diamond-shaped visual element 350, or diamond graph, can include a plurality of segments 358, one or more of which can make up a middle portion 352 as well as upper 354 and lower 356 extremity portions. The diamond graph can also include an actionable value indicator 360. It should be understood that, while the bar graph 250 and the diamond graph 360 are each shown as comprising of a number of discrete segments 258, 358, this is not required. Furthermore, those of skill in the art can recognize a wide variety of variations in shapes, sizes, colors, etc. of the visual elements disclosed in this specification which can be used in various embodiments.

While the visual element 150 of FIG. 1 may be a bar graph, as described herein, many other shapes and embodiments are also possible. For example, the visual element 150 can be any graphical shape or symbol with a reference point about which the graphical shape or symbol extends, expands, or otherwise modulates in at least two directions. In one embodiment, the visual element 150 is a circle (not shown), though other shapes can also be used, whose size increases and decreases in response to changes in a physiological signal, such as a respiratory signal. For example, the circle may have an initial diameter that is indicative of a transition between two or more physiological states. In one embodiment, the diameter of the circle increases during a first physiological state, such as patient inspiration, while the diameter decreases during a second physiological state, such as patient expiration. Therefore, when the diameter of the circle is larger than the initial diameter, an observer can see that the patient is in a first physiological state. When the diameter of the circle is smaller than the initial diameter, an observer can see that the patient is in a second physiological state. Many other types of visual elements 150 are also possible.

Figure 4A:
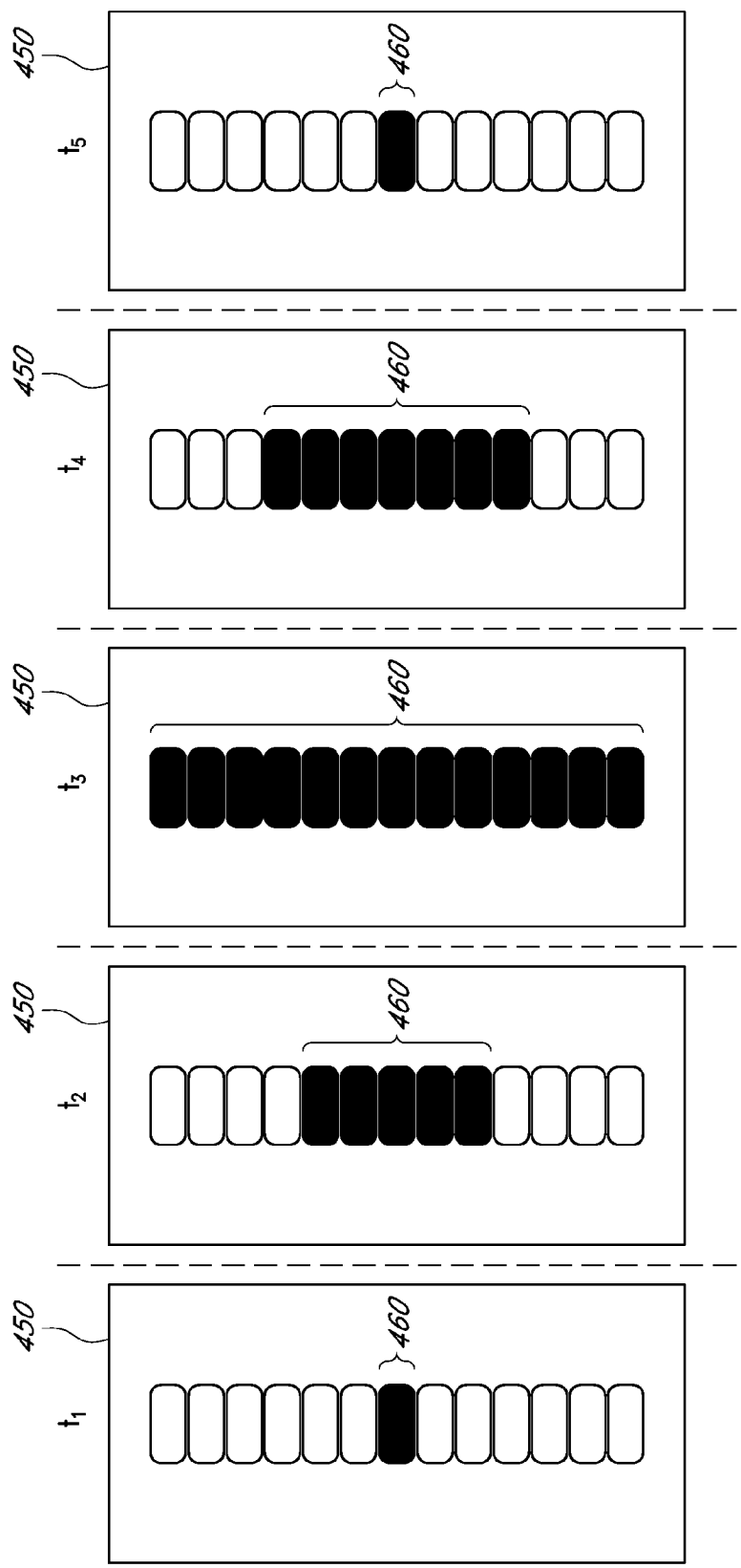
FIG. 4A is an embodiment of a series of depictions of the visual element of FIG. 2 shown at different times as a physiological signal (e.g., a respiratory signal) fluctuates.

FIG. 4A is a series of depictions of the visual element of FIG. 2 shown at different times as a physiological signal (e.g., a respiratory signal) fluctuates. FIG. 4A includes still frames of a bar graph 450 at times t1, t2, t3, t4, and t5 as the value indicator 460 actuates in response to changes in a patient's respiratory signal. In this example, the value indicator 460 represents the acoustic volume of the respiratory sounds picked up by the acoustic sensor 120.

Figure 4B:
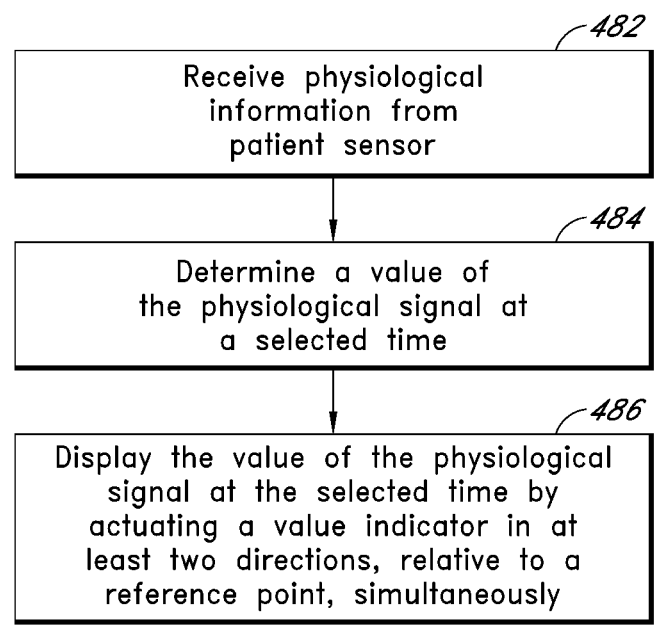
FIG. 4B is an embodiment of a flowchart that further describes the illustrations in FIG. 4A.

FIG. 4B is a flowchart that further describes the illustrations in FIG. 4A. At block 482, a processor (not shown) in a physiological monitoring system (e.g., 105) receives physiological information from a patient sensor (e.g., 120). At block 484, the processor determines the value of the physiological signal at a selected time. At block 486, the processor causes the value of the physiological signal at the selected time to be displayed on a patient monitor (e.g., 110) by actuating a value indicator in at least two directions, relative to a reference point, simultaneously. This process can be performed repeatedly for each of a plurality of selected times, as seen in FIG. 4A.

Returning now to FIG. 4A, at time t1, the value indicator 460 shows that the acoustic volume of the patient's breathing is relatively small. This can occur in a respiratory signal during an instant between inspiration and expiration (or between expiration and inspiration) by a patient where substantially no breathing sound is detected. At time t2, the value indicator 460 has expanded to indicate the detection of a greater acoustic volume. In this embodiment, both the upper and lower extremity portions of the bar graph 450 are representative of relatively greater magnitudes of the acoustic volume of the respiratory signal than is the middle portion of the bar graph 450. Thus, the value indicator expands both in the direction of the upper extremity portion of the bar graph 450 as well as the lower extremity portion, in this case, by a substantially equal amount. At time t3, the value indicator 460 expands even further in both directions and indicates a relatively loud acoustic respiratory sound. Relatively large acoustic respiratory sounds, such as this, are typically detected during the middle portion of a patient inspiratory or expiratory phase. At time t4, the value indicator 460 has contracted somewhat, representing a decrease in the acoustic volume of the patient's respiratory signal. Finally, at time t5, the value indicator 460 contracts to the middle portion of the bar graph 450, indicating that the patient has completed one inspiratory phase and is transitioning to an expiratory phase, or vice versa.

In the embodiment illustrated in FIG. 4A, the middle portion of the bar graph 450 is indicative of a transition between inspiratory and expiratory phases in the patient's respiratory activity. As the patient inhales, the acoustic volume of the patient's breathing sounds increases, causing the value indicator to expand in the direction of both extremity portions of the bar graph 450 until such time as the acoustic volume reaches its peak and begins to taper off, causing the value indicator to contract back toward the middle portion of the bar graph 450. The patient can then begin to exhale, at which point the acoustic volume of the patient's breathing sounds can increase once again and the cycle shown in FIG. 4 can generally repeat itself, though the maximum value detected during inspiratory and expiratory phases, as well as the time to complete each phase, may not be equal. The series of bar graphs 450 shown in FIG. 4 can, therefore, be representative of patient inspiration or expiration. In certain cases it may be desirable to distinguish patient inspiration from expiration. For example, the value indicator 460 could be displayed in green during inspiration and in blue during expiration. In other embodiments, the value indicator 460 could blink during one respiratory phase while remaining solid during the other. Other mechanisms for distinguishing between patient inspiration and expiration in this embodiment are also possible.

A multi-directional visual element such as illustrated and described with respect to FIGS. 2-8A provides several clinical advantages in certain embodiments. For example, clinical monitors typically display a multitude of data related to many different physiological parameters of a patient. Some monitors display several numerical values related to a patient's overall health, such as blood pressure, pulse rate, blood oxygen concentration or saturation, etc. Monitors also often display several graphical images, or waveforms, as well. Although such information can be clinically useful to a medical provider, in some cases the quantity of information provided on a physiological monitor's display can cause confusion. For example, a clinician may be overwhelmed with the quantity of information provided and may not find the particular information desired when quickly glancing at the monitor's display. In such cases it is particularly useful to provide certain types of physiological information with a unique visual element that can be quickly discerned by a clinician. By doing so, the medical practitioner can become accustomed to visualizing particular physiological information (e.g., respiratory information) with a particular visual element (e.g., those described with respect to FIGS. 2-8A). This can allow the medical practitioner to quickly find the information of interest from an information-rich visual display.

Figure 5A:
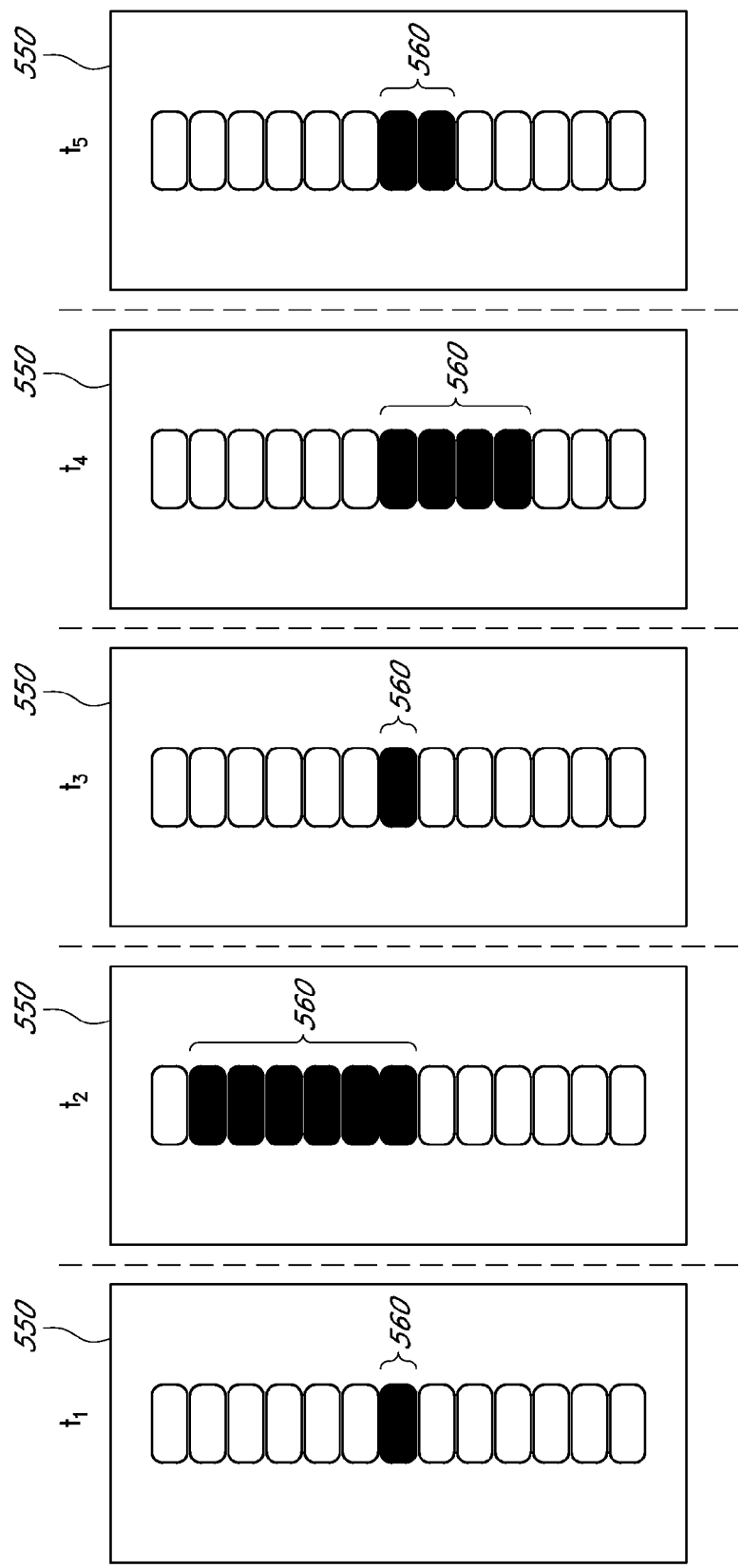
FIG. 5A is an embodiment of a series of depictions of the visual element of FIG. 2 shown at different times as a physiological signal (e.g., a respiratory signal) fluctuates.

FIG. 5A is another example of a series of depictions of the visual element of FIG. 2 shown at different times as a physiological signal (e.g., a respiratory signal) fluctuates. The value indicator 560 indicates the acoustic volume of the respiratory sounds detected by the acoustic sensor 120. Both extremity portions of the bar graph 550 are representative of relatively larger magnitude values of the acoustic volume of the respiratory signal than is the middle portion of the bar graph. However, the value indicator 560 in this embodiment actuates in the region of one of the extremity portions of the bar graph 550 at a time. For example, the upper extremity portion of the bar graph 550 can correspond to a first phase of a physiological event (e.g., the respiratory signal which correspond to a patient inspiratory phase), while the lower extremity portion of the bar graph can correspond to a second phase of a physiological event (e.g., an expiratory phase). Therefore, the value indicator 560 represents different physiological states, phases, conditions, activities, etc. along different directions, or in different regions.

Figure 5B:
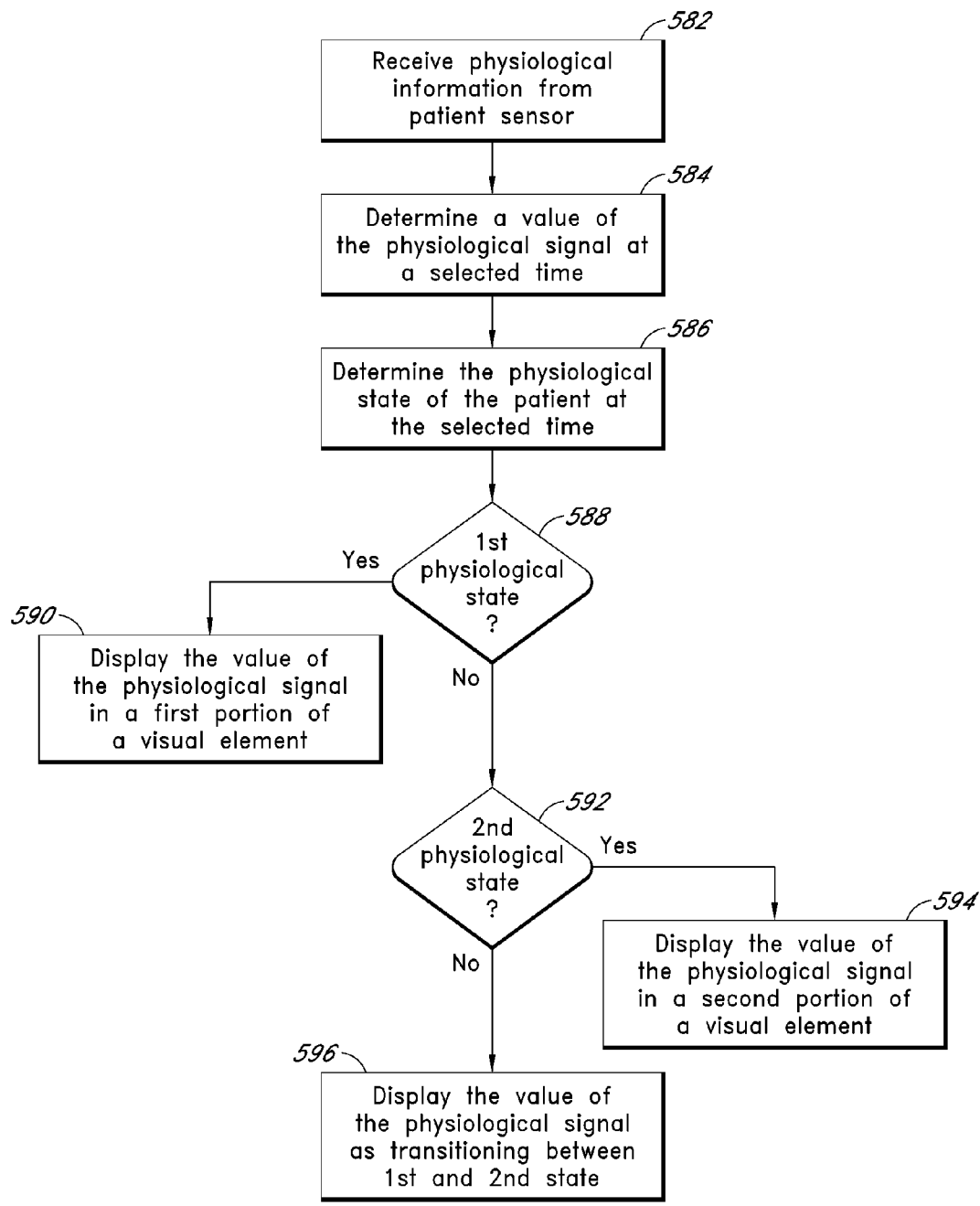
FIG. 5B is an embodiment of a flowchart that further describes the illustrations in FIG. 5A.

FIG. 5B is a flowchart that further describes the illustrations in FIG. 5A. At block 582, a processor (not shown) in a physiological monitoring system (e.g., physiological monitoring system 105 or any other system described herein) receives physiological information from a patient sensor (e.g., patient sensor 120 or any other sensor described herein). At block 584, the processor determines the value of the physiological signal at a selected time. At block 586, the processor determines a physiological state of the patient at the selected time, as represented by the value of the physiological signal at that time. If the patient is in a first physiological state (e.g., inspiration) at decision block 588, then the processor causes the value of the physiological signal to be displayed in a first portion of a visual element. If the patient is in a second physiological state (e.g., expiration) at decision block 592, then the processor causes the value of the physiological signal to be displayed in the second portion of the visual element. If the patient is not in either of the first or second physiological states, then, in some embodiments, it can be assumed that the patient is transitioning between the first and second physiological states, and the value of the physiological signal is displayed accordingly at block 596. This process can be performed repeatedly for each of a plurality of selected times, as seen in FIG. 5A.

Returning now to FIG. 5A, at time t1, the value indicator 560 shows that a relatively small acoustic volume has been detected. Again, during normal respiratory activity this corresponds to a transition between patient inspiration and expiration. At time t2, the value indicator 560 expands in the region of the upper extremity portion of the bar graph 550 to indicate the detection of relatively loud patient inspiration sounds. At time t3, the value indicator 560 contracts back to the middle portion of the bar graph 550, indicating the end of the inspiratory phase. The position of the value indicator 560 at time t4 corresponds to the detection of a moderately loud expiratory signal. Later, at time t5, the acoustic volume of the patient's expiratory action is shown to have decreased somewhat before it can eventually return back to the middle portion of the bar graph 550, indicating the completion of the patient's expiratory phase. As illustrated in FIG. 5A, the acoustic volume of a patient's breathing sounds during inspiratory and expiratory phases does not necessarily reach the same maximum value. Nor are the two respiratory phases necessarily of equal duration.

FIGS. 4A, 4B, 5A, and 5B merely represent two examples of ways in which a value indicator can actuate in response to changes in a patient's respiratory, or other physiological, signal according to different embodiments. In this way, a patient's respiratory activity can be easily monitored by a caregiver observing the respiratory monitor 110. As discussed previously, a patient's respiratory activity can be continuously monitored by an acoustic sensor 120 and transmitted to the patient respiratory monitor 110. The respiratory monitor 110 can include circuitry to sample the acquired continuous time respiratory signal and convert it into a digital representation. This operation results in a discrete series of time samples which approximate the continuous-time respiratory signal. The respiratory monitor 110 can also include a processor to analyze the respiratory signal and to cause a value indicator to actuate in accordance with changes in the respiratory signal over time, as illustrated in FIGS. 4A, 4B, 5A, and 5B.

In some embodiments, one respiratory data point is displayed by a visual element (e.g., visual element 150 or other visual elements described herein) for every time sample of the continuous-time signal. In other words, the value indicator actuation refreshes once for each time sample of the respiratory signal, e.g., if the continuous-time respiratory signal is sampled 60 times per second, the value indicator refreshes 60 times per second as well. However, the series of respiratory data points displayed by a visual element can also be different than the number of time samples that are taken from the continuous-time signal. For example, if the continuous-time respiratory signal is sampled 60 times per second, the value indicator may be configured to only refresh for every third time sample. In other embodiments, a plurality of time samples are combined to form a single value in the series of data points displayed by the visual element. For example, the value indicator can be configured to display a series of data points where each data point represents the average (e.g., a moving average) or median of a group of time samples in order to smooth the actuation of the value indicator. It is also possible for the value indicator to be configured to actuate at a higher rate than the sampling rate of the continuous-time respiratory signal by interpolating between time samples.

Figure 6:
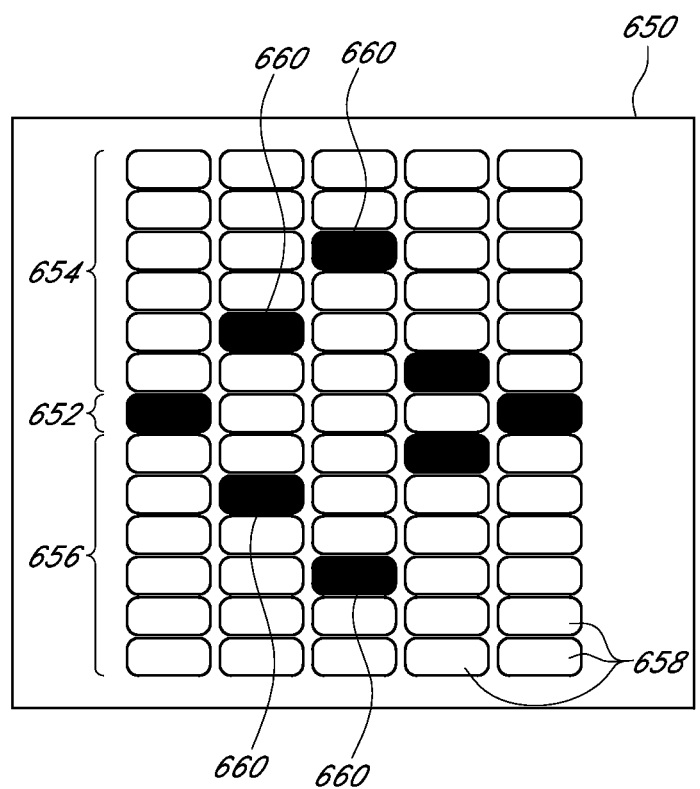
FIG. 6 is an embodiment of a schematic representation of a visual element capable of simultaneously displaying a plurality of values associated with a physiological signal (e.g., a respiratory signal) at a plurality of times.

Some embodiments can be configured to display more than one data point (e.g., a value) at a time. For example, FIG. 6 is a schematic representation of a visual element capable of simultaneously displaying a plurality of values associated with a physiological signal (e.g., a respiratory signal). The visual element 650 includes an array of segments 658. The visual element 650 also includes a middle portion 652, as well as upper 654 and lower 656 extremity portions which are indicative of differing values of a respiratory, or other physiological, signal. Each of the five columns of segments represents a separate value in a series of data points displayed on the visual element 650. For example, the first column of segments can represent the value of a physiological signal at time t1, the second column can represent the value at time t2, etc.

In addition, each column of segments 658 includes a value indicator 660, which actuates in response to changes in a physiological signal as described above. The value indicators 660 in FIG. 6 only have their end points illuminated, rather than all intervening segments 658 as well. In other embodiments, end points and intervening segments 658 are both illuminated. Other types of value indicators are also possible. Each value indicator 660 can be configured to refresh in turn one after another until an end column, e.g., the right-most column, in the visual element 650 has been reached. At this point the pattern may repeat and the value indicator in the opposite end column, e.g., the left-most column, can be refreshed. Other patterns for refreshing the value indicators 660 are also possible. For example, the value indicators 660 can be configured to all refresh simultaneously and hold their respective values until the next refresh time. Since the value indicator 650 shows a plurality of values, it can be configured to show an entire inspiratory or expiratory phase. In other embodiments, the visual element 650 can be configured to display entire respiratory periods, i.e., one inspiratory phase and one expiratory phase, or even several respiratory periods, at once.

Figure 7A:
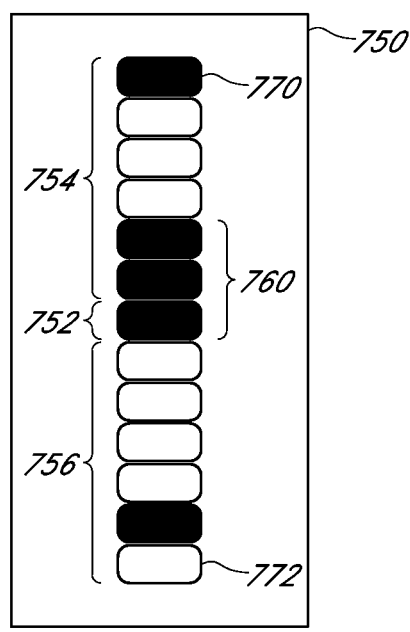
FIG. 7A is an embodiment of a schematic representation of a visual element, which includes peak indicators, for displaying a physiological signal (e.g., a respiratory signal)

In some embodiments, a visual element (e.g., 150) also includes separate indicators to communicate additional information to an observer. For example, FIG. 7A is a schematic representation of a visual element, which includes peak indicators, for displaying a physiological signal (e.g., a respiratory signal). The bar graph 750 includes a middle portion 752, an upper extremity portion 754, and a lower extremity portion 756. The bar graph 750 also includes a value indicator 760 which can be configured to actuate in response to changes in a detected respiratory signal. The bar graph 750 also includes an inspiration peak indicator 770 as well as an expiration peak indicator 772. The peak indicators 770, 772 can be configured to communicate to an observer the maximum magnitude that a patient's respiratory signal has reached during inspiratory and expiratory phases over a pre-determined time period. The peak indicators 770, 772 may be useful to a caregiver as an indication of the history of the patient's breathing activity and may aid in diagnoses or in decision making related to the patient's care.

In one embodiment, the peak indicators 770, 772 of FIG. 7A are portions of the bar graph 750 which have been configured to remain activated (e.g., in a lit up state) to show the maximum values or magnitudes attained by the patient's respiratory signal over a period of time. For example, the peak indicators 770, 772 remain activated even when the current value shown by the value indicator 760 is other than the peak value, or values, represented by the peak indicators

770, 772. For example, in FIG. 7A, the value indicator 760 shows a current inspiratory signal value of a moderate level. The inspiration peak indicator 770, however, shows that the patient's inspiratory signal reached a maximum value represented by the upper most segment of the bar graph 750 within some pre-determined period of time in its history. Likewise, the expiration peak indicator 772 shows the maximum value reached by the patient's expiratory signal over a period of time. In other embodiments, the peak indicator 772 illuminates to a different color than the physiological signal portion displayed on the bar graph 750.

The peak indicators 770, 772 can be configured to actuate to higher levels when new peak values in the patient's respiratory signal are attained. Similarly, the peak indicators 770, 772 may actuate to show smaller values if the patient's breathing activity has trended downward and previously reached peak values have not been met within the most recent pre-determined period of time.

The peak indicators 770, 772 can be configured to show the maximum values or magnitudes attained by a patient's respiratory signal over any period of time in the history of the signal. In one embodiment, for example, the peak indicators 770, 772 show the maximum acoustic volumes reached by a patient's respiratory signal over the course of the past five minutes. In some embodiments, the time period is configured to be adjustable by a caregiver.

Figure 7B:
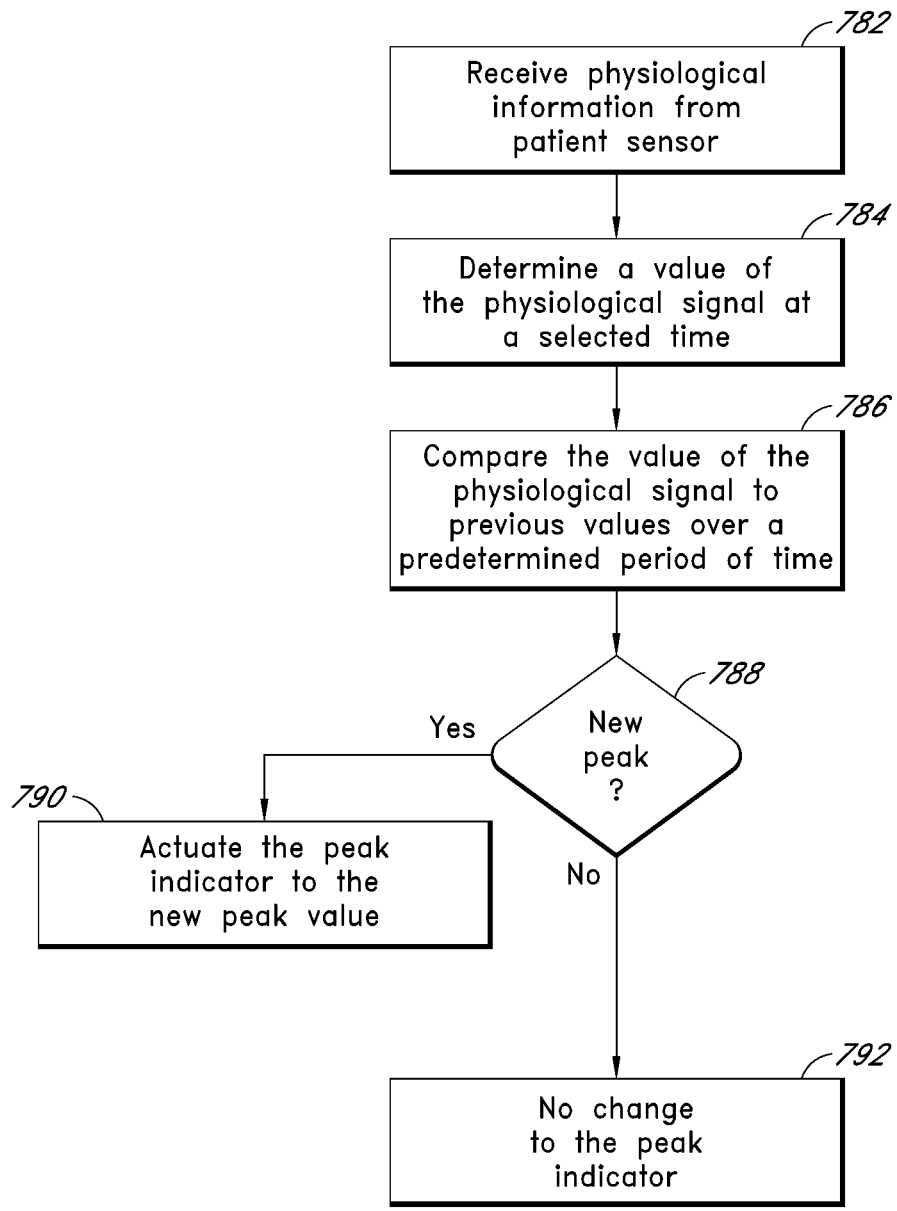
FIG. 7B is an embodiment of a flowchart that further describes the illustrations in FIG. 7A.

FIG. 7B is a flowchart that further describes the illustrations in FIG. 7A. At block 782, a processor (not shown) in a physiological monitoring system (e.g., 105) receives physiological information from a patient sensor (e.g., 120). At block 784, the processor determines the value of the physiological signal at a selected time. At block 786, the processor compares the value of the physiological signal at the selected time to previous values over a predetermined period of time. If the value of the physiological signal at the selected time reflects a new peak value, then the processor proceeds from decision block 788 to block 790 where it actuates a corresponding peak indicator 770, 772 to reflect the new peak value. Otherwise, at block 792, the processor does not change the peak indicator 770, 772. This process can be performed over for each new value of the physiological signal.

As illustrated in FIG. 7A, the peak indicators 770, 772 may be a segment, or other portion, of the bar graph 750. In these embodiments, the peak indicators 770, 772 can be displayed in different colors from the value indicator 760 for clarity in identifying the peak values or magnitudes. In other embodiments, the peak indicators 770, 772 may be configured to blink on and off. In still other embodiments, the peak indicators 770, 772 may be located adjacent the bar graph rather than being a part of the bar graph and may include an icon, arrow, or other graphical element. Other arrangements are also possible and can be recognized by those of skill in the art.

Figure 8A:
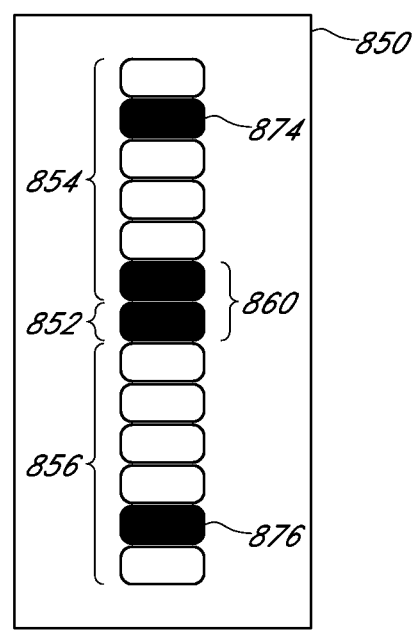
FIG. 8A is an embodiment of a schematic representation of a visual element, which includes goal indicators, for displaying a physiological signal (e.g., a respiratory signal)

Some embodiments include additional types of indicators. For example, FIG. 8A is a schematic representation of a visual element, which includes goal indicators, for displaying a physiological signal (e.g., a respiratory signal). The bar graph 850 includes goal indicators 874, 876 which represent a value of a respiratory, or other physiological, signal for which a patient is to strive to reach. In the case of respiratory signals, this type of goal indicator can be beneficial to patients in need of exercising their lungs while recovering from surgery or as therapy for some other medical condition. Certain embodiments include an inspiratory goal indicator 874 and an expiratory goal indicator 876. Each of these goal indicators 874, 876 is a visual cue that indicates to a patient a target value to try to reach in his or her breathing.

In FIG. 8A, for example, if the value indicator 860 is understood to show the instant where the patient's inspiratory phase has reached its peak value or magnitude, which in this case is relatively low, the patient can see from the bar graph that he or she must breathe more deeply in order to reach the target value represented by the inspiratory goal indicator 874. Thus, the goal indicators 874, 876 help a patient strive to reach a desired level of breathing activity, whether for the purposes of recovery, testing, or some other reason. In some embodiments, the goal indicators 874, 876 are set and reconfigured by a caregiver, such as a doctor or nurse, or by the patient himself.

The goal indicators 874, 876 can be a segment, or other portion, of the bar graph 850, such as an LED, LCD, and/or an icon, color, sound, or combination thereof. In such cases it may be desirable to display the goal indicators in a color other than that used for the value indicator 860. In some embodiments, the goal indicators 874, 876 are configured to blink, for example, when the patient achieves the targeted value of the physiological signal. In still other embodiments, the goal indicators 874, 876 are accompanied by an audible indicator which sounds when the patient reaches the targeted goal. Many other configurations for displaying the goal indicators and signaling when the goal has been met are possible as well.

Figure 8B:
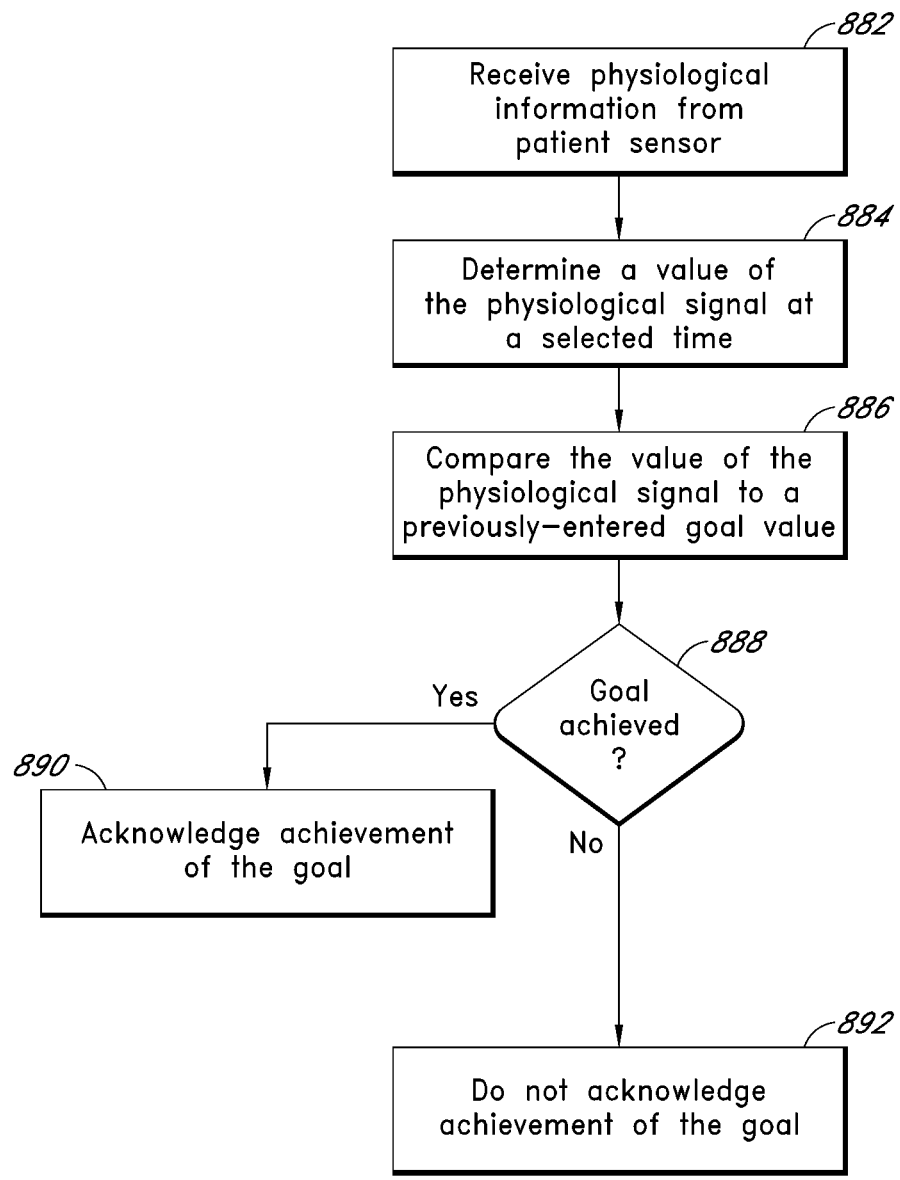
FIG. 8B is an embodiment of a flowchart that further describes the illustrations in FIG. 8A.

FIG. 8B is a flowchart that further describes the illustrations in FIG. 8A. At block 882, a processor (not shown) in a physiological monitoring system receives physiological information from a patient sensor. At block 884, the processor determines the value of the physiological signal at a selected time. At block 886, the processor compares the value of the physiological signal at the selected time to a goal value that has been previously inputted by a caregiver or by the patient. If the value of the physiological signal at the selected time meets or exceeds the goal value, then the processor proceeds from decision block 888 to block 890 where it causes an acknowledgement that the goal has been reached to be given. This acknowledgement can be, for example, an audible sound. Otherwise, at block 892, the processor causes no such acknowledgement to be given. This process can be performed over for each new value of the physiological signal.

Figure 9:
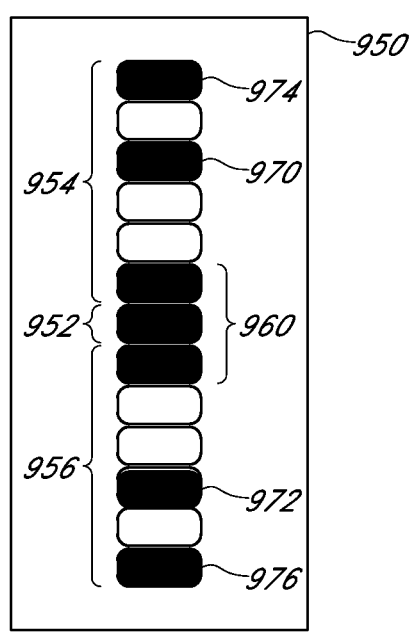
FIG. 9 is an embodiment of a schematic representation of a visual element, which includes a plurality of types of indicators, for displaying a physiological signal (e.g., a respiratory signal).

Some embodiments include more than one type of additional indicator beyond a value indicator. This is represented in FIG. 9, which is a schematic representation of a visual element that includes a plurality of types of indicators for displaying a physiological signal (e.g., a respiratory signal). The bar graph 950 includes peak indicators 970, 972, as well as goal indicators 974, 976. The bar graph 950 also includes a middle portion 952, an upper extremity portion 954, a lower extremity portion 956, and a value indicator 960 which is configured to actuate in response to changes in a detected physiological signal. In FIG. 9, it can be seen that the patient's respiratory signal has reached a peak value or magnitude marked by the peak indicators 970, 972 that still falls short of the patient's targeted goal, as marked by the goal indicators 974, 976. Thus the patient, or a caregiver, can recognize that the patient should continue to strive to breathe more deeply.

Additional types of indicators can also be included in various embodiments. As is described herein, these indicators can be configured as portions of a bar graph, for example. They may also be numbers, letters, or symbols located adjacent a visual element such as a bar graph. In some embodiments, indicators described herein are actionable in response to changes in a physiological signal. For example, in addition to the peak and goal indicators described above, a bar graph 950, or other type of visual element (e.g., visual element 150 or any other visual element described herein), can include indicators to show average values of a patient's respiratory signal during inspiratory or expiratory phases. The bar graph 950 could also include short-term peak indicators which are configured to represent value or magnitude peaks attained during a relatively short-term history of the patient's respiratory activity as well as long-term peak indicators which are configured to represent value or magnitude peaks attained over the course of a longer period of time. It should be apparent to those of skill in the art that the bar graph 950, or other type of visual element, can also include many other types of indicators to communicate to an observer any type of information related to a physiological signal.

Some embodiments include visual elements with additional information in the form of text, numbers, images, icons, or symbols, for example. In one embodiment, a visual element includes numbers which indicate the respiratory rate (e.g., breaths per minute) and/or respiratory period (e.g., seconds per breath) of a patient. A visual element can also include a numerical depiction of a value related to a physiological signal or an indication of signal quality (see FIG. 11). Other types of information that would be recognized by those in the skill as having a relationship to a physiological signal or of being of some benefit to a caregiver can also be included with the visual element.

In some embodiments, the patient monitor 110 also includes a speaker or other device capable of producing audible sounds. The patient monitor 110 can be configured to output a sound that varies in response to changes in a physiological signal. For example, the patient monitor 110 can output a sound that increases and decreases in volume in response to changes in a physiological signal. In one embodiment, the sound increases as the value or magnitude of the signal increases, and decreases as the value or magnitude of the signal decreases. In some embodiments, the pitch of the sound varies in response to changes in the physiological signal. For example, the pitch of the sound may increase as the value or magnitude of the signal increases, and may decrease as the value or magnitude of the signal decreases. Some embodiments produce "beeps" or other sounds that occur closer together or further apart in time in response to changes in the physiological signal. Some embodiments of the physiological monitor 110 output one sound during inspiration and a different sound during expiration of a respiratory signal as a non-visual indication of the different phases of the respiratory signal.

In some embodiments, the speaker is also configured to emit alarms when a patient enters into a dangerous or undesirable condition. For example, if the physiological monitor 110 detects a temporary cessation in the patient's breathing, such as might occur in a patient with apnea, the speaker can emit an alarm. The speaker may also be configured to emit an alarm if the patient's respiratory rate or depth of respiration decreases beyond a certain threshold.

Figure 10:
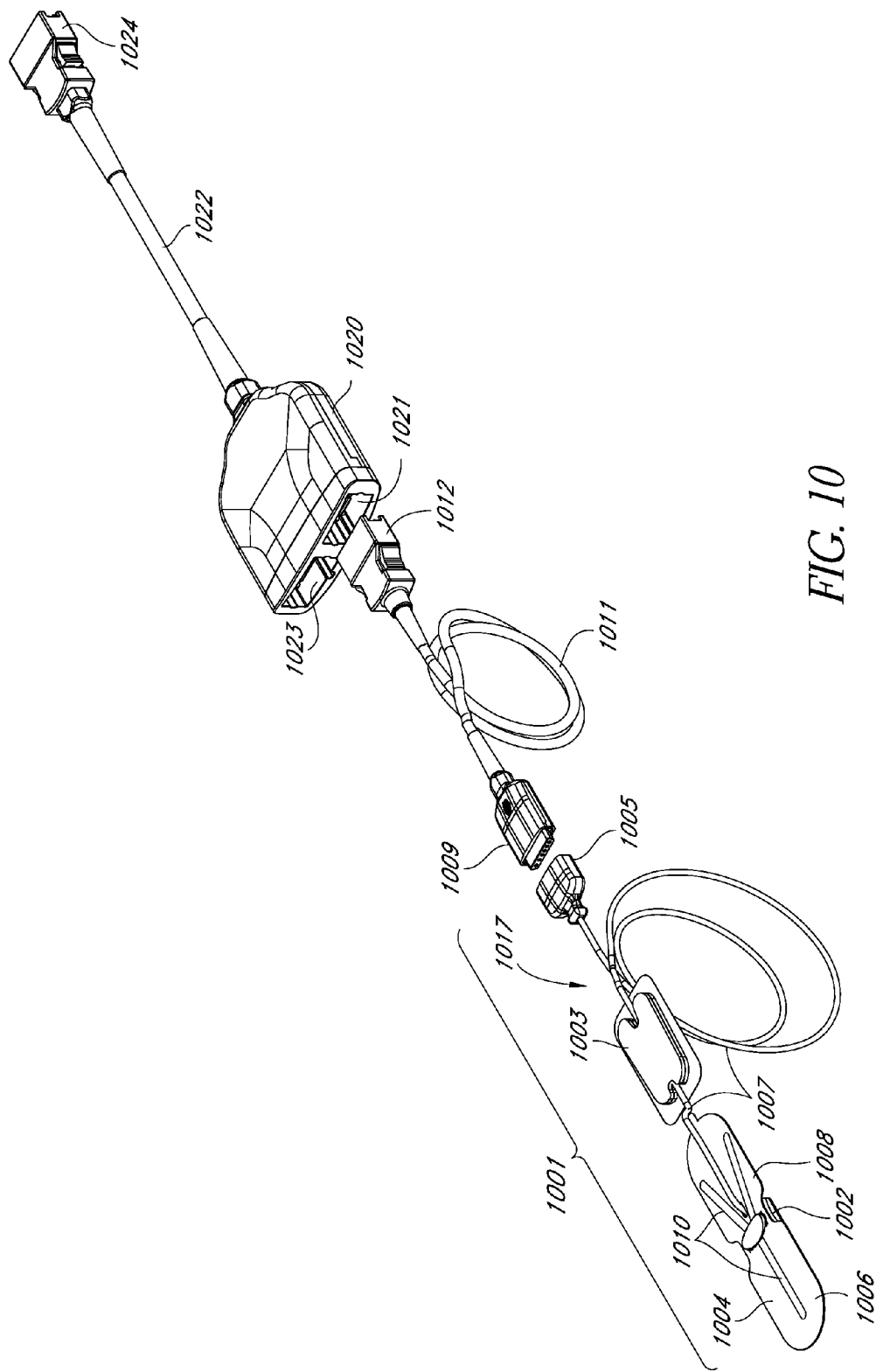
FIG. 10 is an embodiment of a top perspective view illustrating an embodiment of a sensor assembly and cable.

FIG. 10 illustrates an embodiment of a sensor system 1000 including a sensor assembly 1001 and a monitor cable 1011 suitable for use with any of the physiological monitors and cables described herein. The sensor assembly 1001 includes a sensor 1015, a cable assembly 1017, and a connector 1005. The sensor 1015, in one embodiment, includes a sensor subassembly 1002 and an attachment subassembly 1004. The cable assembly 1017 of one embodiment includes a sensor 1007 and a patient anchor 1003. A sensor connector subassembly 1005 is connected to the sensor cable 1007.

The sensor connector subassembly 1005 can be removably attached to an instrument cable 1011 via an instrument cable connector 1009. The instrument cable 1011 can be attached to a cable hub 1020, which includes a port 1021 for receiving a connector 1012 of the instrument cable 1011 and a second port 1023 for receiving another cable. The hub 1020 is an example of the splitter cable described above, and as such, can include decoupling circuitry. In certain embodiments, the second port 1023 can receive a cable connected to an optical sensor (e.g., a pulse oximetry sensor) or other sensor. In addition, the cable hub 1020 could include additional ports in other embodiments for receiving additional cables. The hub includes a cable 1022 which terminates in a connector 1024 adapted to connect to a physiological monitor (not shown).

The sensor connector subassembly 1005 and connector 1009 can be configured to allow the sensor connector 1005 to be straightforwardly and efficiently joined with and detached from the connector 1009. Embodiments of connectors having connection mechanisms that can be used for the connectors 1005, 1009 are described in U.S. patent application Ser. No. 12/248,856 (hereinafter referred to as "the '856 Application"), filed on Oct. 9, 2008, which is incorporated in its entirety by reference herein. For example, the sensor connector 1005 could include a mating feature (not shown) which mates with a corresponding feature (not shown) on the connector 1009. The mating feature can include a protrusion which engages in a snap fit with a recess on the connector 1009. In certain embodiments, the sensor connector 1005 can be detached via one hand operation, for example. Examples of connection mechanisms can be found specifically in paragraphs [0042], [0050], [0051], [0061]-[0068] and [0079], and with respect to FIGS. 8 A-F, 13 A-E, 19 A-F, 23 A-D and 24 A-C of the '856 Application, for example.

The sensor connector subassembly 1005 and connector 1009 can reduce the amount of unshielded area in and generally provide enhanced shielding of the electrical connection between the sensor and monitor in certain embodiments. Examples of such shielding mechanisms are disclosed in the '856 Application in paragraphs [0043]-[0053], [0060] and with respect to FIGS. 9A-C, 11A-E, 13A-E, 14A-B, 15A-C, and 16A-E, for example.

In an embodiment, the acoustic sensor assembly 1001 includes a sensing element, such as, for example, a piezoelectric device or other acoustic sensing device. The sensing element can generate a voltage that is responsive to vibrations generated by the patient, and the sensor can include circuitry to transmit the voltage generated by the sensing element to a processor for processing. In an embodiment, the acoustic sensor assembly 1001 includes circuitry for detecting and transmitting information related to biological sounds to a physiological monitor. These biological sounds can include heart, breathing, and/or digestive system sounds, in addition to many other physiological phenomena. The acoustic sensor 1015 in certain embodiments is a biological sound sensor, such as the sensors described herein. In some embodiments, the biological sound sensor is one of the sensors such as those described in the '883 Application. In other embodiments, the acoustic sensor 1015 is a biological sound sensor such as those described in U.S. Pat. No. 6,661,161, which is incorporated by reference herein in its entirety. Other embodiments include other suitable acoustic sensors.

The attachment sub-assembly 1004 includes first and second elongate portions 1006, 1008. The first and second elongate portions 1006, 1008 can include patient adhesive (e.g., in some embodiments, tape, glue, a suction device, etc.). The adhesive on the elongate portions 1006, 1008 can be used to secure the sensor subassembly 1002 to a patient's skin. One or more elongate members 1010 included in the first and/or second elongate portions 1006, 1008 can beneficially bias the sensor subassembly 1002 in tension against the patient's skin and reduce stress on the connection between the patient adhesive and the skin. A removable backing can be provided with the patient adhesive to protect the adhesive surface prior to affixing to a patient's skin.

The sensor cable 1007 can be electrically coupled to the sensor subassembly 1002 via a printed circuit board ("PCB") (not shown) in the sensor subassembly 1002. Through this contact, electrical signals are communicated from the multi-parameter sensor subassembly to the physiological monitor through the sensor cable 1007 and the cable 1011.

In various embodiments, not all of the components illustrated in FIG. 10 are included in the sensor system 1000. For example, in various embodiments, one or more of the patient anchor 1003 and the attachment subassembly 1004 are not included. In one embodiment, for example, a bandage or tape is used instead of the attachment subassembly 1004 to attach the sensor subassembly 1002 to the measurement site. Moreover, such bandages or tapes can be a variety of different shapes including generally elongate, circular and oval, for example. In addition, the cable hub 1020 need not be included in certain embodiments. For example, multiple cables from different sensors could connect to a monitor directly without using the cable hub 1020.

Additional information relating to acoustic sensors compatible with embodiments described herein, including other embodiments of interfaces with the physiological monitor, are included in U.S. patent application Ser. No. 12/044,883, filed Mar. 7, 2008, entitled "Systems and Methods for Determining a Physiological Condition Using an Acoustic Monitor," (hereinafter referred to as "the '883 Application"), the disclosure of which is hereby incorporated by reference in its entirety. An example of an acoustic sensor that can be used with the embodiments described herein is disclosed in U.S. patent application Ser. No. 12/643,939, incorporated above.

Freshness Indicator

Figure 11:
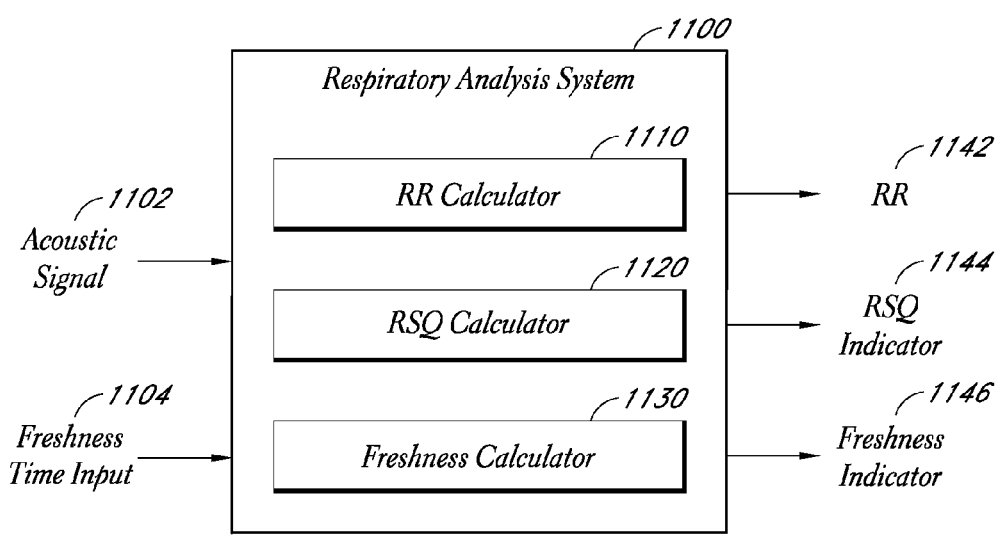
FIG. 11 illustrates an embodiment of a respiratory analysis system.

Referring to FIG. 11, a respiratory analysis system 1100 is shown. The respiratory analysis system 1100 can calculate one or more parameters related to an acoustic signal obtained from a patient. The respiratory analysis system 1100 can calculate, among other parameters, respiratory rate (sometimes referred to as RR), respiratory signal quality (RSQ), and freshness of the respiratory rate calculation. Advantageously, in certain embodiments, the respiratory analysis system 1100 can output data and/or indicators reflecting one or more of these parameters, thereby assisting clinicians with assessing a health status of a patient.

The respiratory analysis system 1100 includes three example modules in the depicted embodiment. These modules include a respiratory rate calculator 1110, an RSQ calculator 1120, and a freshness calculator 1130. Each of these modules can include hardware and/or software for performing certain tasks. An acoustic signal 1102 is received by the respiratory analysis system 1100 and is used by one or more of the modules to perform these tasks. The acoustic signal 1102 can be obtained from an acoustic sensor, such as any of the sensors described above, coupled to a living patient.

The respiratory rate calculator 1100 can analyze the acoustic signal 1102 to determine a respiratory rate measurement for the patient. The respiratory rate measurement can vary with time. The respiratory rate calculator 1100 can output the respiratory rate measurements 1142 for presentation to a clinician. For example, the respiratory rate calculator 1100 can output the respiratory rate measurements 1142 to a display or to another clinician device over a network (such as a nurse's station computer in a hospital).

The RSQ calculator 1120 can calculate an objective measure of the quality of the acoustic signal 1102. The RSQ calculator 1120 can, for instance, quantitatively determine how corrupted the acoustic signal 1102 is by noise, how similar the acoustic signal 1102 is to known waveform characteristics of respiratory signals, and the like. Based at least in part on this analysis, the RSQ calculator 1120 can output an RSQ indicator 1144 that reflects the calculated quality of the acoustic signal 1102. The RSQ calculator 1120 can output the RSQ indicator 1144 to a display or to another clinician device over a network. Advantageously, in certain embodiments, the RSQ indicator 1144 can be implemented as any of the visual indicators or elements described above. For instance, the RSQ indicator 1144 can be a bidirectional bar graph. As signal quality changes, the bidirectional bar graph could change accordingly.

The RSQ indicator 1144 could be a unidirectional bar graph instead of a bidirectional bar graph. The RSQ indicator 1144 can also be a binary indicator, indicating low or high RSQ. The RSQ indicator 1144 could also be a numerical value, such as a percentage or the like. In another embodiment, the RSQ indicator 1144 can be an occurrence indicator, such as the occurrence indicator described in U.S. Pat. No. 6,996,427, titled "Pulse Oximetry Data Confidence Indicator," filed Dec. 18, 2003, the disclosure of which is hereby incorporated by reference in its entirety. Any combination of the indicators described herein and/or other types of indicators could be used.

The freshness calculator 1130 calculates a freshness or relevance of the respiratory rate measurement 1142. In some situations, the respiratory rate calculator 1110 and/or the RSQ calculator 1120 might determine that a calculated respiratory rate measurement 1142 is invalid, of low quality, or cannot be measured. An invalid respiratory rate measurement 1142 can be, for example, a measurement that is not physiological possible (such as a measurement that is too high). An invalid measurement can also be a measurement that changes rapidly over a short period of time. One option when invalid or other low quality measurements occur is to discard the invalid or low quality respiratory rate value and not display a new measurement until a valid or higher quality value is obtained. However, not displaying a respiratory rate value (or showing zero) can confuse a clinician if the patient is still breathing.

Thus, instead of displaying no (or zero) value in low quality signal conditions, the respiratory rate calculator 1110 can continue to output the previous respiratory rate measurement 1142 for a certain amount of time. This amount of time can be determined by the freshness calculator 1130. The freshness calculator 1130 can include a counter, timer, or the like that increments (or decrements) as soon as a low or invalid signal condition is detected by the respiratory rate calculator 1110 or the RSQ calculator 1120. When the freshness calculator 1130 determines that a certain amount of time has elapsed, for example, by comparison with a predetermined threshold time value, the freshness calculator 1130 can cause the respiratory rate calculator 1110 to output a zero or no respiratory rate value. Conversely, if while the freshness calculator 1130 is incrementing (or decrementing) the counter the respiratory rate calculator 1110 produces a valid or higher quality respiratory rate measurement 1142, the freshness calculator 1130 can reset the counter.

The amount of time elapsed before the freshness calculator 1130 outputs a zero or no respiratory rate value can be user-configurable. The respiratory analysis system 1100 can, for instance, output a user interface control on a display of a patient monitor that enables a clinician to adjust the freshness period. This input by a clinician can then be updated in the freshness calculator 1130. The respiratory analysis system 1100 can provide a user interface element on a display or the like for the clinician to input the freshness timer input 1104.

The freshness calculator 1130 can output a freshness indicator 1146 that reflects a freshness of the respiratory rate measurement 1142. The freshness calculator 1130 can output the freshness indicator 1146 to a display or to another clinician device over a network. The freshness indicator 1146 can be a light, for instance, that turns on when the freshness calculator 1130 is incrementing (or decrementing) the counter. The light could also change color as the counter is incremented (or decremented). The freshness indicator 1146 could also be a bar, a number, or any other visual element. The freshness indicator 1146 could also be an audible indicator, such as an audible alarm. The audible indicator can increase in intensity as the counter is incremented (or decremented).

In another embodiment, the freshness indicator 1146 can be implemented as a flashing version of a parameter value or other value indicator. For example, any numeric value of a parameter can flash to reflect lack of, or a decrease in, freshness. The bidirectional display bar described above can also flash to reflect the lack of freshness. The flashing of the parameter or other value indicator can increase (or decrease) in rate until a defined time period has expired. After this time period has expired, a zero value can be displayed for the parameter. Moreover, when the freshness period has expired, an alarm can be triggered.

In yet another embodiment, the freshness indicator 1146 and the RSQ indicator 1144 are implemented together, for example, as follows. The RSQ indicator 1144 can generally indicate changes in signal quality of a respiration or acoustic signal. The freshness of a respiratory rate measurement 1142 can be calculated as described above. Instead of outputting a separate indicator, the calculated freshness can be used to adjust the output of the RSQ indicator 1144. If a respiratory rate measurement 1142 is less fresh, for instance, the RSQ indicator 1144 can reflect this as a lower value, a lower bar (or bars), or the like. In one embodiment, the RSQ indicator 1144 is lowered by some percentage, such as 5%, 10%, 20%, or some other percentage. In other embodiments, the RSQ indicator 1144 gradually drops toward some minimum value (such as zero) as the freshness decreases.

Any combination of these features can be used for the freshness indicator 1146, as well as others.

Figure 12:
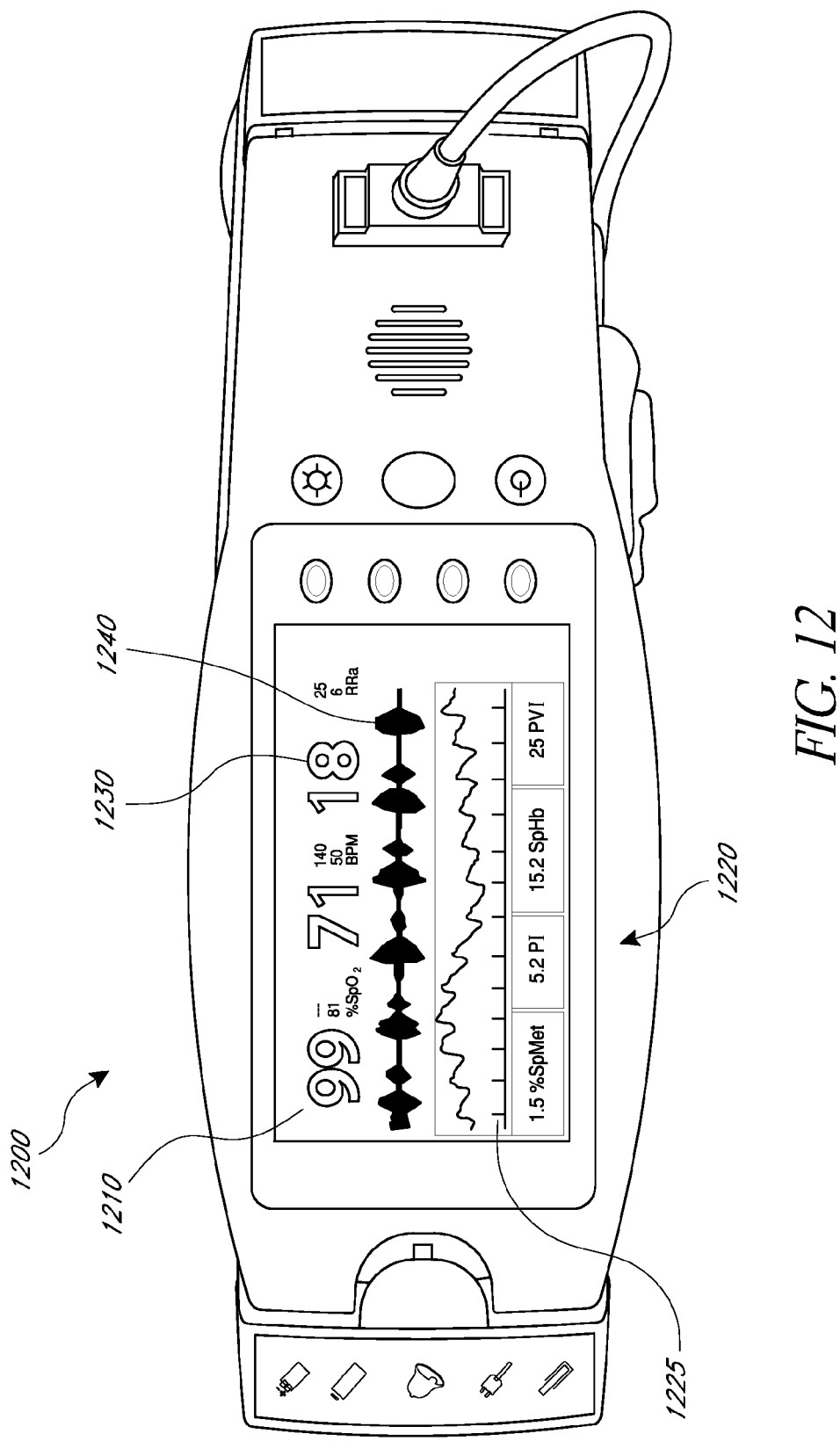
FIG. 12 illustrates an embodiment of a physiological monitor having a respiration display.

FIG. 12 illustrates an embodiment of a patient monitor 1200 having a respiration display. The patient monitor 1200 can include any of the features described above. Further, the patient monitor 1200 can implement any of the displays or other features described above. In the depicted embodiment, the patient monitor 1200 displays an example respiration waveform.

The patient monitor 1200 displays parameter indicators for several physiological parameters in the depicted embodiment. Some of these parameter indicators include an oxygen saturation indicator 1210, hemoglobin, perfusion index, plethysmograph variability index, and other indicators 1220, and an occurrence graph 1225 reflecting signal quality for an optical signal.

Further, the patient monitor 1200 displays an example respiratory rate indicator 1230 that reflects values of a patient's respiratory rate. This value can be obtained using any of the respiratory rate measurement methods described above. Advantageously, in the depicted embodiment, the patient monitor 1200 also includes a respiration waveform 1240. This respiration waveform 1240 can represent a patient's time-domain respiration signal or an envelope of the respiration signal over a period of time. The respiration waveform 1240 can be bidirectional or unidirectional in some embodiments. The depicted patient monitor 1200 illustrates a bidirectional respiration waveform 1240. A unidirectional respiration waveform 1240 might include excursions in a single direction (e.g., positive or negative) from an axis.

The respiration waveform 1240 can reflect an actual respiration signal, providing a clinician with more information about a patient's breathing pattern than just the respiratory rate indicator 1230 alone. The respiration waveform 1240 can enable a clinician to diagnose patient problems by observing, for instance, heights and widths of peaks in the respiratory waveform 1240, irregularities in the respiratory waveform 1240, spikes of activity in the respiratory waveform 1240, general low activity in the respiratory waveform 1240, some combination of the same, or the like.

It should be noted that although several embodiments herein have described a bidirectional display, a unidirectional display can be used instead to represent respiratory parameters.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Depending on the embodiment, certain acts, events, or functions of any of the methods described herein can be performed in a different sequence, can be added, merged, or left out all together (e.g., not all described acts or events are necessary for the practice of the method). Moreover, in certain embodiments, acts or events can be performed concurrently, e.g., through multi-threaded processing, interrupt processing, or multiple processors or processor cores, rather than sequentially.

The various illustrative logical blocks, modules, circuits, and algorithm steps described in connection with the embodiments disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

The blocks of the methods and algorithms described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, a hard disk, a removable disk, a CD-ROM, or any other form of computer-readable storage medium known in the art. An exemplary storage medium is coupled to a processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments of the inventions described herein can be embodied within a form that does not provide all of the features and benefits set forth herein, as some features can be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A method of displaying physiological information on a physiological monitor, the method comprising:
   by a processor:
      receiving an acoustic respiration signal from an acoustic respiratory sensor coupled with a patient;
      outputting a value indicator to a display of the physiological monitor to visually communicate one or more characteristics associated with the acoustic respiration signal to an observer, the value indicator configured to represent an envelope amplitude of the respiration signal and respiratory signal quality, wherein the value indicator includes a reference position representative of a transition between alternating phases of inspiration and expiration in the respiration signal;
      expanding the value indicator from the reference position in two directions simultaneously in response to increasing values of the envelope amplitude during each alternating phase of inspiration and expiration;
      contracting the value indicator opposite the two directions simultaneously toward the reference position in response to falling values of the envelope amplitude during each alternating phase of inspiration and expiration;
      calculating a measure of the respiratory signal quality by analyzing the acoustic respiration signal; and
      setting a characteristic of the value indicator to reflect the measure of the respiratory signal quality.

2. The method of claim 1, further comprising:
   detecting a change in the measure of the respiratory signal quality; and
   changing the characteristic of the value indicator to reflect the change in the measure of the respiratory signal quality.

3. The method of claim 2, wherein said changing the characteristic of the value indicator comprises transitioning the value indicator between dark and lit states.

4. The method of claim 2, wherein said changing the characteristic of the value indicator comprises changing a color of the value indicator.

5. The method of claim 2, wherein said changing the characteristic of the value indicator comprises causing the value indicator to flash.

6. The method of claim 1, wherein said calculating the measure of the respiratory signal quality comprises quantitatively determining how corrupted the respiration signal is by noise.

7. The method of claim 1, wherein said calculating the measure of the respiratory signal quality comprises determining a level of similarity between the respiration signal and known waveform characteristics of respiration signals.

8. The method of claim 1, wherein said expanding the value indicator comprises expanding the value indicator in first and second directions that are substantially opposite one another.

9. The method of claim 1, further comprising determining that a calculated respiratory signal measurement is of invalid respiratory signal quality.

10. The method of claim 9, further comprising discarding the calculated respiratory signal measurement of invalid respiratory signal quality and setting the characteristic of the value indicator to reflect a previously calculated respiratory signal measurement.

11. The method of claim 10, further comprising not displaying a new calculated respiratory signal measurement until obtaining a calculated respiratory signal measurement of valid respiratory signal quality.

12. The method of claim 10, further comprising calculating a freshness of the previously calculated respiratory signal measurement and adjusting the characteristic of the value indicator based at least partly on the freshness.

13. The method of claim 1, further comprising visually altering the value indicator to distinguish between inspiration and expiration.

14. A physiological monitor comprising:
   a processor configured to receive physiological information comprising a respiration signal from one or more sensors coupled with a patient; and a display comprising a visual element configured to represent an envelope amplitude of the respiration signal and a respiratory signal quality of the respiration signal, the visual element comprising a value indicator, wherein the value indicator includes a reference position representative of a transition between alternating phases of inspiration and expiration in the respiration signal;

wherein the processor is configured to:
expand the value indicator from the reference position in two directions simultaneously in response to increasing values of the envelope amplitude during each alternating phase of inspiration and expiration;
contract the value indicator opposite the two directions simultaneously toward the reference position in response to falling values of the envelope amplitude during each alternating phase of inspiration and expiration,
calculate a measure of the respiratory signal quality, and
change a characteristic of the value indicator to reflect the measure of the respiratory signal quality.

15. The physiological monitor of claim 14, wherein, to change the characteristic of the value indicator, the processor is configured to change a color of the value indicator in response to the measure of the respiratory signal quality.

16. The physiological monitor of claim 14, wherein the value indicator comprises a bidirectional bar graph.

17. The physiological monitor of claim 14, wherein the value indicator comprises a segmented display.

18. The physiological monitor of claim 14, wherein the characteristic of the value indicator comprises a binary indicator.

19. The physiological monitor of claim 18, wherein the characteristic of the binary indicator indicates whether the measure of the quality of the respiration signal is low or high.

20. The physiological monitor of claim 14, further comprising visually altering the value indicator to distinguish between inspiration and expiration.

* * * * *